United States Patent
Jezek et al.

(10) Patent No.: US 9,744,242 B2
(45) Date of Patent: Aug. 29, 2017

(54) STABLE AQUEOUS FORMULATIONS OF ADENOVIRUS VECTORS

(71) Applicant: Arecor Limited, Little Chesterford, Saffron Walden (GB)

(72) Inventors: Jan Jezek, Wellingborough (GB); Angela Buckler, Saffron Walden (GB)

(73) Assignee: Arecor Limited, Cambridge (GB)

( * ) Notice: Subject to any disclaimer, the term of this patent is extended or adjusted under 35 U.S.C. 154(b) by 0 days.

(21) Appl. No.: 14/988,138

(22) Filed: Jan. 5, 2016

(65) Prior Publication Data

US 2016/0199496 A1   Jul. 14, 2016

Related U.S. Application Data

(62) Division of application No. 14/208,919, filed on Mar. 13, 2014, now Pat. No. 9,254,332.

(60) Provisional application No. 61/793,461, filed on Mar. 15, 2013.

(51) Int. Cl.

| | |
|---|---|
| *A61K 47/38* | (2006.01) |
| *C07K 14/005* | (2006.01) |
| *C12N 7/00* | (2006.01) |
| *A61K 39/235* | (2006.01) |
| *A61K 47/36* | (2006.01) |
| *C12N 15/86* | (2006.01) |
| *A61K 47/32* | (2006.01) |
| *A61K 9/00* | (2006.01) |
| *A61K 47/18* | (2017.01) |
| *A61K 48/00* | (2006.01) |

(52) U.S. Cl.
CPC ............ *A61K 47/38* (2013.01); *A61K 9/0019* (2013.01); *A61K 39/235* (2013.01); *A61K 47/36* (2013.01); *C07K 14/005* (2013.01); *C12N 7/00* (2013.01); *C12N 15/86* (2013.01); *A61K 47/183* (2013.01); *A61K 47/32* (2013.01); *A61K 48/0008* (2013.01); *C12N 2710/10343* (2013.01); *C12N 2710/10351* (2013.01)

(58) Field of Classification Search
None
See application file for complete search history.

(56) References Cited

U.S. PATENT DOCUMENTS

| | | |
|---|---|---|
| 6,251,678 B1 | 6/2001 | Volkin et al. |
| 7,456,009 B2 | 11/2008 | Evans et al. |
| 7,888,097 B2 | 2/2011 | Wu et al. |
| 9,254,332 B2 | 2/2016 | Jezek et al. |
| 2008/0299182 A1 | 12/2008 | Zhang et al. |

FOREIGN PATENT DOCUMENTS

WO    WO 2014/140645 A1    9/2014

OTHER PUBLICATIONS

Kim, H.-J., et al., "Efficient Transduction with Recombinant Adenovirus in EBV-transformed B Lymphoblastoid Cell Lines," *Journal of Biochemistry and Molecular Biology*; 37(3): 376-382 (May 2004).
"AdenoExpressTM," Retrieved from the internet on May 11, 2014; https://web.archive.org/web/20040305075914/http://www.adenovirus.com/products/adenoexpress (2004).
De Belder, A. N., "Dextran," *Amersham Biosciences; Edition AA*: 7-64; (2003).
Park, H., et al., "Fabrication of cross-linked alginate beads using electrospraying for adenovirus delivery," *Int'l Journal of Pharmaceutics*; 427: 417-425 (2012).
International Search Report for International Application No. PCT/GB2014/050826, European Patent Office, Netherlands, mailed Jul. 31, 2014.

*Primary Examiner* — Benjamin P Blumel
(74) *Attorney, Agent, or Firm* — Sterne, Kessler, Goldstein & Fox, P.L.L.C.

(57) ABSTRACT

The present invention is based on the surprising discovery that the inclusion of an anionic polymer in the adenovirus formulation enhances long-term stability of the vector composition. An aqueous formulation comprising an adenovirus vector and at least one anionic polymer is provided, together with methods of the preparation of a storage stable adenovirus aqueous formulation.

22 Claims, 15 Drawing Sheets

STABLE AQUEOUS FORMULATIONS OF ADENOVIRUS VECTORS

CROSS REFERENCE TO RELATED APPLICATIONS

This application is a divisional of U.S. patent application Ser. No. 14/208,919, filed Mar. 13, 2014, which claims benefit of U.S. Provisional Patent Application No. 61/793,461, filed Mar. 15, 2013 each of which is incorporated herein by reference.

BACKGROUND OF THE INVENTION

Field of the Invention

The present invention relates to aqueous formulations comprising an adenovirus vector and at least one anionic polymer. The present invention further relates to methods for the preparation of a storage stable adenovirus aqueous formulation.

Background

Recombinant adenovirus vectors are becoming increasingly important for use in vaccine development and gene therapy applications. Adenoviruses for gene therapy traditionally have been formulated and stored at less than −60° C. to ensure good virus stability during storage. When formulated conventionally as liquid compositions, such vectors are insufficiently stable during prolonged storage and/or at ambient temperature. There are some limited reports of aqueous formulations of adenovirus with stability data.

U.S. Pat. No. 7,456,009 describes adenovirus formulations with improved stability when stored at 2° C.-8° C. The formulations comprise a buffer, sugar, salt, divalent cation, non-ionic surfactant, and a free-radical scavenger.

U.S. Pat. No. 7,880,097 describes adenovirus formulation with bulking agents, cryoprotectants, and lyoprotectants in both aqueous and lyophilized formulations, allowing storage at 4° C. for up to six months.

There remains a need for adenovirus vector formulations having at least a twelve-month shelf-life, and preferably at least a twenty-four months shelf-life, at 2° C.-8° C. and for at least three months at 25° C.

BRIEF SUMMARY OF THE INVENTION

The present invention is directed to an aqueous formulation comprising an adenovirus vector and at least one anionic polymer.

The present invention is also directed to a method for preparing a storage stable adenovirus aqueous formulation, comprising forming a mixture of an adenovirus vector and at least one anionic polymer.

In some embodiments, the at least one anionic polymer is selected from the group consisting of dextran sulfates, carboxymethyl cellulose, polyglutamate, polyaspartate, and salt forms thereof, for example sodium salts. The at least one anionic polymer may be at a concentration ranging from about 0.5 mg/mL to about 10 mg/mL.

In one embodiment, the at least one anionic polymer is dextran sulfate. The dextran sulfate may have an average molecular weight between about 3000 Da and 30000000 Da. In some embodiments, the dextran sulfate is selected from the group consisting of: dextran sulfate having an average molecular weight of about 5000 Da, dextran sulfate having an average molecular weight between about 6500 Da and about 10000 Da, dextran sulfate having an average molecular weight between about 9000 Da and about 20000 Da, and dextran sulfate having an average molecular weight between about 500000 Da and about 3000000 Da.

In certain embodiments, the formulation comprises one dextran sulfate with an average molecular weight between about 6500 Da and about 10000 Da at a concentration ranging from about 4 mg/mL to about 6 mg/mL and one dextran sulfate with an average molecular weight between about 500000 Da and about 3000000 Da at a concentration ranging from about 0.9 mg/mL to about 6 mg/mL.

In some embodiments, the at least one anionic polymer is sodium carboxymethyl cellulose. The sodium carboxymethyl cellulose may have an average molecular weight between about 20000 Da and about 1000000 Da, preferably an average molecular weight of about 90000 Da.

In some embodiments, the formulation further comprises at least one buffer. In some embodiments, the at least one buffer is a displaced buffer having a ionizable group with a pKa value at least one unit higher or lower than the pH of the formulation and has no ionizable group with a pKa value within one unit of the pH of the formulation. In some embodiments, the formulation comprises a combination of two displaced buffers preferably TRIS and benzoate ion, each at a concentration ranging from about 5 mM to about 50 mM, preferably from about 5 mM to about 20 mM. Displacement buffer systems are discussed, for example, in US Pat. Pub. No. 2010/0028372A1 and in WO2008/084237, the contents of each of which are incorporated by reference herein in their entirety.

In some embodiments, the pH of the formulation is between 5 and 8, between 5.5 and 7.5, or preferably between 6 and 7.

In certain embodiments, the formulation further comprises a tonicity modifier selected from the group consisting of 1,2-propanediol, glycerol, mannitol, sorbitol, sucrose, lactose, maltose, and trehalose. Preferably, the tonicity modifier is sucrose. In some embodiments, the tonicity modifier is at a concentration sufficient to provide osmolarity between about 100 mOsm/l and about 1000 mOsm/l, preferably between about 200 mOsm/l and about 500 mOsm/l.

In some embodiments, the formulation further comprises a non-ionic surfactant selected from the group consisting of polysorbates and poloxamers. Examples of suitable polysorbates include, but are not limited to, polysorbate 80, polysorbate 60, polysorbate 40, and polysorbate 20. Examples of suitable poloxamers include, but are not limited to, poloxamer 182, poloxamer 188, poloxamer 331, poloxamer 338, and poloxamer 407. In some embodiments, the non-ionic surfactant is polysorbate 80 at a concentration ranging from 0.05 mg/mL to about 0.6 mg/mL.

In some embodiments, the formulation further comprises EDTA at a concentration of less than about 5 mM, such as less than about 1 mM, or preferably ranging from about 0.05 mM to about 0.5 mM.

In some embodiments, the formulation further comprises at least one salt of a divalent cation selected from the group consisting of $MgCl_2$, $MgSO_4$, $CaCl_2$, $CaSO_4$, $ZnCl_2$, $ZnSO_4$, $MnCl_2$, and $MnSO_4$. Preferably, the salt is $MgCl_2$ at a concentration ranging from about 0.5 mM to about 5 mM, preferably of about 1.5 mM.

In some embodiments, the formulation further comprises polyvinyl alcohol at a concentration ranging from about 1 mg/mL to about 10 mg/mL, preferably about 5 mM.

In a particular embodiment, the formulation comprises an adenovirus vector, a dextran sulfate with an average molecular weight between about 6500 Da and about 10000 Da, a dextran sulfate with an average molecular weight between about 500000 Da and about 3000000 Da, a combination of TRIS and benzoate ion as—displaced buffers, EDTA, sucrose, polysorbate 80, and polyvinyl alcohol. The pH of this formulation is about 6.

In another particular embodiment, the formulation comprises an adenovirus vector, a dextran sulfate with an average molecular weight between about 6500 Da and about 10000 Da, a dextran sulfate with an average molecular weight between about 500000 Da and about 3000000 Da, a combination of TRIS and benzoate ion as displaced buffers, EDTA, sucrose, and polysorbate 80. The pH of this formulation is about 7.

In still another particular embodiment, the formulation comprises an adenovirus vector, a dextran sulfate with an average molecular weight between about 6500 Da and about 10000 Da, a dextran sulfate with an average molecular weight between about 500000 Da and about 3000000 Da, a combination of TRIS and benzoate ion as a displaced buffer, sucrose, and polysorbate 80. The pH of this formulation is about 6.5.

In preferred embodiments, the formulation maintains high infectivity when stored for twenty-four months at a temperature ranging from 2° C. to 8° C. or for three months at a temperature of 25° C. In some embodiments, the formulation loses less than 2 log infectivity, preferably less than 1 log infectivity, or more preferably less than 0.5 log infectivity of the starting infectivity when stored for twenty-four months at a temperature ranging from 2° C. to 8° C. or for three months at a temperature of 25° C. In one embodiment the log infectivity is measured by Fluorescence Activated Cell Sorter (FACS) assay. In another embodiment the log infectivity is measured by $TCID_{50}$ assay.

In certain embodiments, the formulation is a pharmaceutical formulation suitable for administration by injection or infusion, e.g., intramuscular, intravenous, subcutaneous or transdermal. For example, the pharmaceutical formulation can be used as a prophylactic vaccine or in gene therapy. In some embodiments, the gene therapy is cancer gene therapy. In some embodiments, the injection is directly into tumor cells.

BRIEF DESCRIPTION OF THE DRAWINGS/FIGURES

Figure 10A:
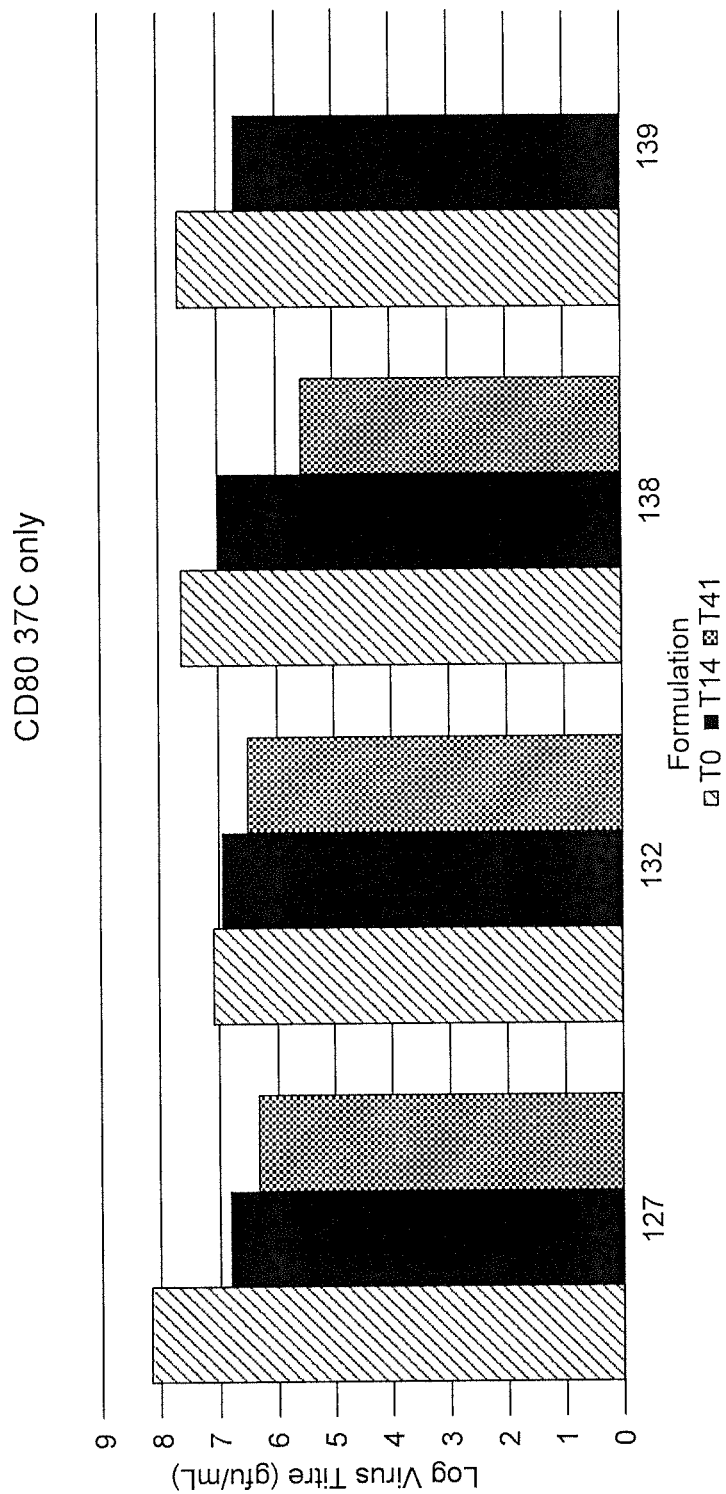

FIG. 10A compares the infectivity of adenovirus formulations with Ad5CD80 system and an incubation temperature of 37° C.

Figure 10B:
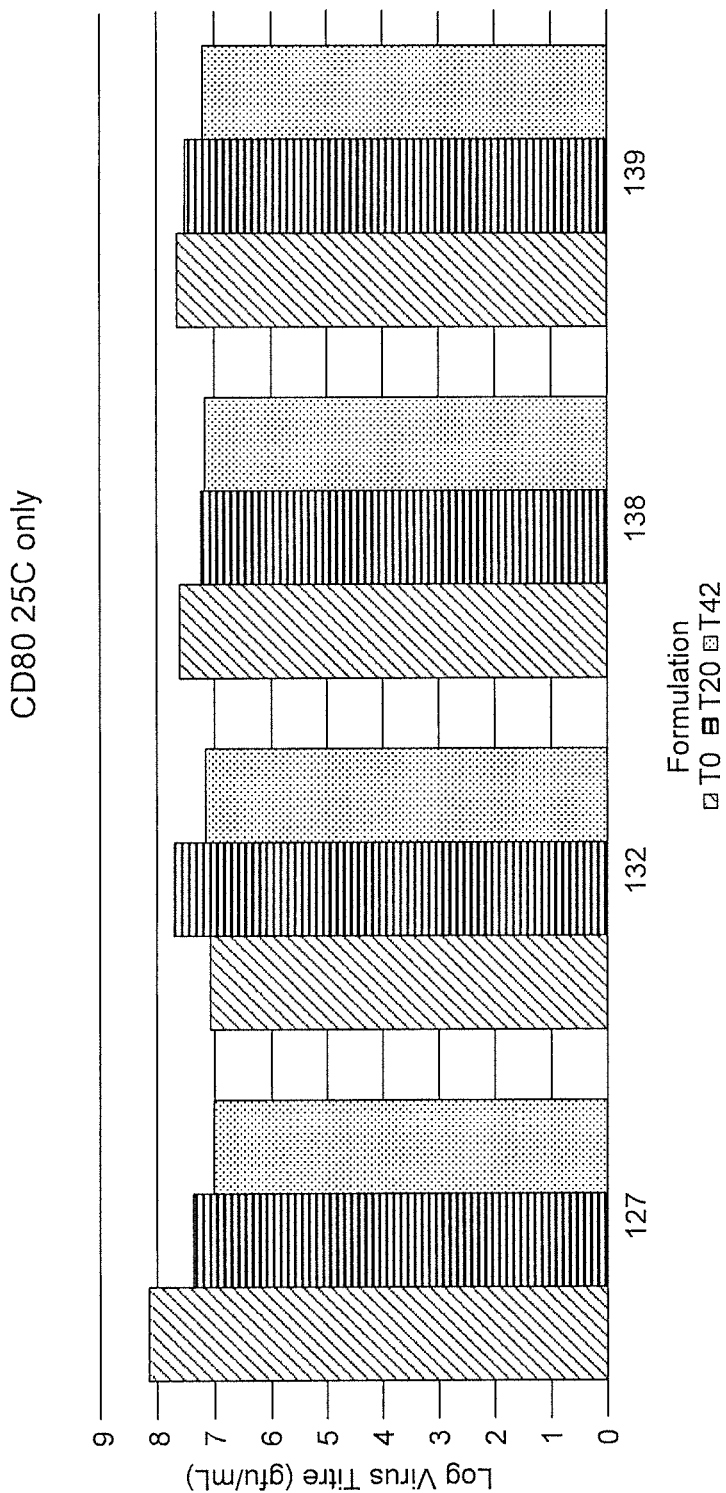

FIG. 10B compares the infectivity of adenovirus formulations with Ad5CD80 system and an incubation temperature of 25° C.

Figure 11A:
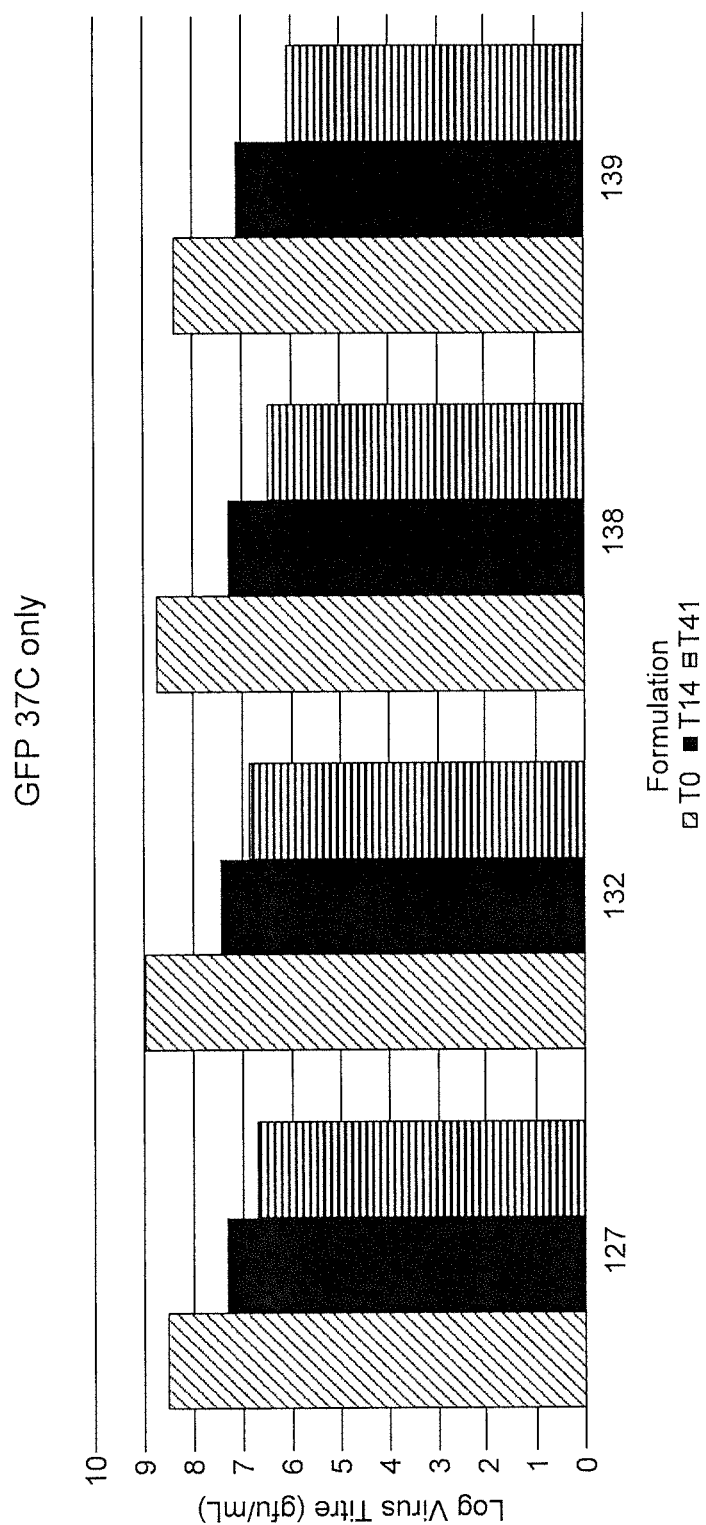

FIG. 11A compares the infectivity of adenovirus formulations with Ad5GFP system and an incubation temperature of 37° C.

Figure 11B:
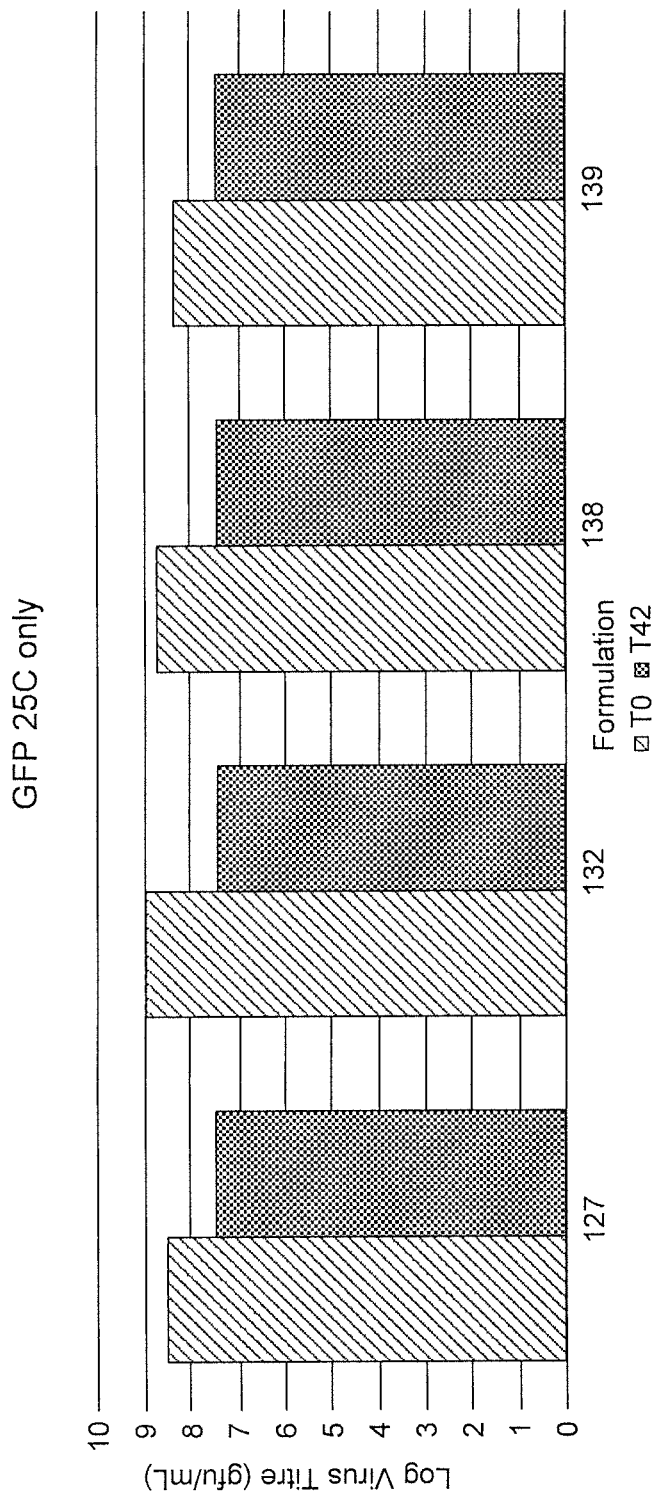

FIG. 11B compares the infectivity of adenovirus formulations with Ad5GFP system and an incubation temperature of 25° C.

DETAILED DESCRIPTION OF THE INVENTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

Unless otherwise defined, all technical and scientific terms used herein have the meaning commonly understood by one skilled in the art to which this invention belongs. All publications, patent applications, patents, and other references mentioned herein are incorporated by reference in their entirety.

As used herein, the singular terms "a" and "the" are synonymous and used interchangeably with "one or more" and "at least one," unless the language and/or context clearly indicates otherwise.

Throughout the specification, use of the term "about" with respect to any quantity is contemplated to include that quantity. For example, "about 0.5 mg/mL" is contemplated herein to include "0.5 mg/mL," as well as values understood in the art to be approximately 0.5 mg/mL with respect to the entity described.

The present invention addresses the need for stable aqueous formulations of adenovirus vectors produced for administration by, e.g., intramuscular injection. The advantages of the present invention are improvement in the thermal stability of such formulations, which has a number of benefits including (i) improvement of shelf life and (ii) ease of storage, transportation and use outside of frozen conditions. Specifically, the present invention is expected to fulfill target product characteristics of shelf life of at least twelve months and preferably twenty-four months at 2-8° C. or for three months at 25° C.

Aqueous Adenovirus Vector Formulations

The present invention is directed to an aqueous formulation comprising an adenovirus vector and at least one anionic polymer. The present invention is based on the surprising discovery that the inclusion of an anionic polymer in the formulation enhances long-term stability of the vector composition.

In some embodiments, the adenovirus is a human adenovirus. In some embodiments, the human adenovirus is a serotype from a subgroup which shows negligible or no tumor growth in animals, such as subgroup C (Ad1, Ad2, Ad5 and Ad6), subgroup D (Ad8, Ad9, Ad10, Ad13, Ad15, Ad17, Ad19, Ad20, Ad22, Ad23, Ad24, Ad25, Ad26, Ad27, Ad28, Ad29, Ad30, Ad32, Ad33, Ad36, Ad37, Ad38, Ad39, Ad42, Ad43, Ad44, Ad45, Ad46, and Ad4), subgroup B (Ad3, Ad7, Ad11, Ad14, Ad16, Ad21, Ad34, and Ad35) and subgroup E (Ad4). For an exhaustive adenovirus classification scheme, see *Fundamental Virology*, 3$^{rd}$ Edition, Chapter 30, page 980, Ed. Fields, et al. 1996, Lippincott-Raven. In some embodiments, the serotype is Ad5 or Ad35 as a single vector, maintaining a concentration in an aqueous solution in the range from about $1\times10^7$ to about $1\times10^{13}$ vp/ml (virus particles/milliliter), from about 1×10⁷ vp/mL to about 1×10¹² vp/mL, or from about 1×10⁷ vp/mL to about 1×10¹⁰ vp/mL.

The term "anionic polymer," as used herein, has its ordinary meaning as understood by those skilled in the art and thus includes, by way of non-limiting example, any polymer with a negative net charge. In some embodiments, the anionic polymer has a repeating subunit which includes, for example, an ionized carboxyl, phosphate or sulfate group having a negative net charge. In some embodiments, the anionic polymer is a polymer of a natural origin with a negative net charge, on which modifications such as enzymatic or chemical fragmentation or derivatization have been performed. Not being bound by any particular theory, the anionic polymer can associate with the fibers and knob proteins on the surface of the adenovirus, protect these components from detrimental interactions, and thus increase stability of the formulation.

Examples of suitable anionic polymers include, but are not limited to, dextran sulfate, keratan sulfate, heparin, salts of hyaluronic acid, salts of colominic acid, chondroitin sulfate, carrageenan, glucomannan, salts of carboxymethyl cellulose, salts of alginic acid, salts of pectinic acid, salts of pectic acid, agar, carboxylic acid salts of polysaccharides, polyglutamate, polyaspartate, salts of poly(galacturonic acid), salts of acrylic acid polymers and copolymers, salts of methacrylic acid polymers and copolymers, poly(vinyl sulfate), as well as fragments or derivatives thereof. Examples of suitable salts associated with anionic polymers include, but are not limited to, sodium, potassium, calcium, zinc, magnesium or ammonium salts, or organic counter ions including substituted ammonium or guanidinium ions.

In some embodiments, the at least one anionic polymer is selected from the group consisting of dextran sulfates, carboxymethyl cellulose, polyglutamate, polyaspartate, and salts form thereof, for example sodium salts. In some embodiments, the at least one anionic polymer is at a concentration ranging from about 0.5 mg/mL to about 10 mg/mL.

In some embodiments, the at least one anionic polymer is dextran sulfate. Dextran sulfate is a complex glucan (polysaccharide) formed by units of glucose molecules each of which contains approximately two sulfate group as shown in the following formula:

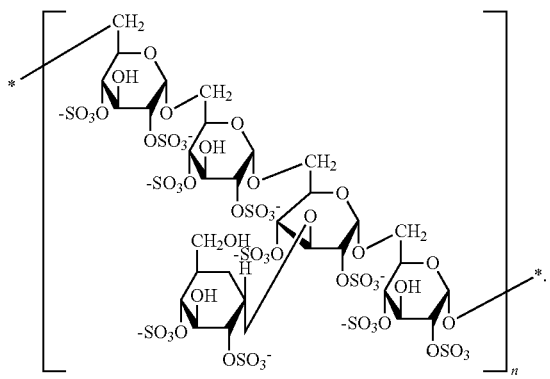

Dextran sulfate is prepared by means of dextran sulfation and subsequent purification by means of methods well-known by the person skilled in the art.

In some embodiments, the dextran sulfate has an average molecular weight between about 3000 Daltons ("Da") and about 3000000 Da. In some embodiments, the dextran sulfate has an average molecular weight between about 6500 Da and about 10000 Da. In some embodiments, the dextran sulfate with an average molecular weight between about 6500 Da and about 10000 Da is at a concentration ranging from about 4 mg/mL to about 6 mg/mL. In some embodiments, the dextran sulfate has an average molecular weight between about 500000 Da and about 3000000 Da. In some embodiments, the dextran sulfate with an average molecular weight between about 500000 Da and about 3000000 Da is at a concentration ranging from 0.9 mg/mL to about 6 mg/mL. In some embodiments, the dextran sulfate is selected from the group consisting of dextran sulfate having an average molecular weight of about 5000 Da, dextran sulfate having an average molecular weight between about 6500 Da and about 10000 Da, dextran sulfate having an average molecular weight between about 9000 Da and about 20000 Da, and dextran sulfate having an average molecular weight between about 500000 Da and about 3000000 Da.

In some embodiments, the formulation comprises one anionic polymer. In some embodiments, the formulation comprises a mixture of anionic polymers. For example, a combination of dextran sulfate of different molecular weights can be used. In some embodiments, the formulation comprises one dextran sulfate with an average molecular weight between about 6500 Da and about 10000 Da and one dextran sulfate has an average molecular weight between about 500000 Da and about 2000000 Da.

In some embodiments, the at least one anionic polymer is sodium carboxymethyl cellulose. In some embodiments, the sodium carboxymethyl cellulose has an average molecular weight between about 20000 Da and 1000000 Da, between about 50000 Da and 800000 Da, or between 90000 Da and 700000 Da. In some embodiments, the sodium carboxymethyl cellulose has an average molecular weight of about 90000 Da.

In some embodiments, the formulation further comprises at least one buffer. The buffer can be either a conventional buffer or a displaced buffer. A typical aqueous adenovirus solution is formulated in a conventional buffer. Examples of a conventional buffer include, but are not limited to, phosphate, citrate, histidine, succinate, acetate, and glycine. The term "conventional buffer," as used herein, is defined as any chemical species with $pK_a$ less than one unit but preferably less than 0.5 units away from pH of the formulation as measured at the intended temperature range of storage of the formulation which possesses a buffering capacity for the adenovirus. The term "displaced buffer," as used herein, is defined as any additive present in a formulation of specified pH which is capable of exchanging protons and has a $pK_a$ value(s) at least 1 unit, or at least 2 units, or at least 3 units more or less than the pH of the formulation at the intended temperature range of storage of the formulation. In one embodiment, the formulation contains one displacement buffer with a pKa value at least one unit more than the pH of the formulation and at least one displacement buffer with a pKa value at least one unit less than the pH of the formulation at the intended temperature range of the storage of the formulation. The art of applying displaced buffers to formulations of biologicals is described in WO 2008/084237, the contents of which are incorporated herein by reference in their entirety. WO 2008/084237 describes the importance of displaced buffers, and the difference between conventional and displaced buffers. In some embodiments, the at least one buffer is a displaced buffer having an ionizable group with a pKa value at least one unit higher or lower than the pH of the formulation and having no ionizable group with a pKa value within one unit of the pH of the formulation.

Examples of compounds that can be usefully incorporated into the adenovirus formulation as additives and that may, subject to the pH of the formulation, function as displaced buffers are known and include, but are not limited to, histidine, maleate, sulphite, cyclamate, hydrogen sulphate, serine, arginine, lysine, asparagine, methionine, threonine, tyrosine, isoleucine, valine, leucine, alanine, glycine, tryptophan, gentisate, salicylate, glyoxylate, aspartame, glucuronate, aspartate, glutamate, tartrate, gluconate, lactate, glycolic acid, adenine, succinate, ascorbate, benzoate, phenylacetate, gallate, cytosine, p-aminobenzoic acid, sorbate, acetate, propionate, alginate, urate, 2-(N-morpholino) ethanesulphonic acid, bicarbonate, bis(2-hydroxyethyl)iminotris(hydroxymethyl)methane, N-(2-acetamido)-2, iminodiacetic acid, 2-[(2-amino-2-oxoethyl)amino]ethanesulphonic acid, piperazine, N,N'-bis(2-ethanesulphonic acid), phosphate, N,N-bis(2-hydroxyethyl)-2, aminoethanesulphonic acid, 3-[N,N-bis(2-hydroxyethyl)amino]-2, hydroxypropanesulphonic acid, triethanolamine, piperazine-N,N'-bis(2, hydroxypropanesulphonic acid), tris(hydroxymethyl)aminomethane, N-tris(hydroxymethyl)glycine, N-tris(hydroxymethyl)methyl-3-aminopropanesulphonic acid, ammonium ion, borate, 2-(N-cyclohexylamino)ethanesulphonic acid, 2-amino-2-methyl-1-propanol, palmitate, creatine, creatinine, and salts thereof. The particular choice of the compound will depend on pH of the formulation.

In some embodiments, the buffer is selected from the group consisting of tris(hydroxymethyl)aminomethane (TRIS), benzoate ion, and a combination thereof. Benzoic acid or its salts, such as sodium or potassium salt, can be used as the source of benzoate ion. Either TRIS base or TRIS hydrochloride can be used as a source of TRIS. In some embodiments, the buffer comprises TRIS and benzoate ion. The concentration of each buffer is usually in the range between about 1 mM and 100 mM, for example between about 5 mM and about 50 mM, or between about 5 mM and about 20 mM.

In most embodiments, the pH of the formulation is between 5 and 8. In some embodiments, the pH of the formulation is between 5.5 and 7.5. In certain embodiments, the pH of the formulation is between 6 and 7.

In some embodiments, the formulation further comprises a tonicity modifier. A purpose of including a tonicity modifier in the formulation is to attain the desired ionic strength or osmolarity. Examples of the tonicity modifier include, but are not limited to, an inorganic salt, an amino acid, and a sugar or sugar alcohol. In some embodiments, the tonicity modifier is an inorganic salt which is a combination of sodium, potassium, calcium, or ammonium cation, with chloride, sulfate nitrate, lactate, succinate, acetate, maleate, or lactate anion. In some embodiments, the tonicity modifier is an amino acid selected from the group consisting of histidine, glycine, arginine, and methionine. In some embodiments, the tonicity modifier is a sugar or sugar alcohol selected from the group consisting of 1,2-propanediol, glycerol, mannitol, sorbitol, sucrose, lactose, maltose, and trehalose. In some embodiments, the tonicity modifier is sucrose.

The aqueous formulations of the present invention cover a wide range of osmolarity, including hypotonic, isotonic, and hypertonic formulations. In some embodiments, the formulation is substantially isotonic. In some embodiments, the tonicity modifier is at a concentration sufficient to provide osmolarity between about 100 mOsm/l and about 1000 mOsm/l. In some embodiments, the tonicity modifier is at a concentration sufficient to provide osmolarity between about 200 mOsm/l and about 500 mOsm/l. In some embodiments, the tonicity modifier is at a concentration sufficient to provide osmolarity between about 250 mOsm/l and about 350 mOsm/l. In some embodiments, the formulation is intended for administration to a subject by intramuscular or subcutaneous injection, and the osmolarity of the formulation is selected to minimize pain upon injection. Contributions to ionic strength or osmolarity may come from ions produced by the buffering compound as well as from the ions of non-buffering salts.

In some embodiments, the formulation further comprises a surfactant. In some embodiments, the surfactant is a non-ionic surfactant. In some embodiments, the non-ionic surfactant is selected from the group consisting of polysorbates and poloxamers. Examples of polysorbates include, but are not limited to, polysorbate 20, polysorbate 40, polysorbate 60, and polysorbate 80. Examples of poloxamers include, but are not limited to, poloxamer 182, poloxamer 188, poloxamer 331, poloxamer 338, and poloxamer 407. In some embodiments, the non-ionic surfactant is polysorbate 80. In some embodiments, the polysorbate 80 is at a concentration ranging from about 0.05 mg/mL to about 0.6 mg/mL. Not being bound by any particular theory, the addition of the non-ionic surfactant can decrease the surface tension of the aqueous formulation, reduce absorption to container surfaces and increase the adenovirus stability.

In some embodiments, the formulation further comprises ethylenediaminetetraacetic acid anion (EDTA). In some embodiments, EDTA is at a concentration of less than about 5 mM. In some embodiments, EDTA is at a concentration of less than about 1 mM. In some embodiments, EDTA is at a concentration ranging from about 0.05 mM to about 0.5 mM.

In further embodiments, the formulation comprises at least one salt of a divalent cation. In some embodiments, the at least one salt of a divalent cation is selected from the group consisting of $MgCl_2$, $MgSO_4$, $CaCl_2$, $CaSO_4$, $ZnCl_2$, $ZnSO_4$, $MnCl_2$, and $MnSO_4$. In some embodiments, the at least one salt of a divalent cation is at a concentration ranging from about 0.5 mM to about 5 mM. In some embodiments, the at least one salt of a divalent cation is at a concentration of about 1.5 mM. In some embodiments, the at least one salt of a divalent cation is $MgCl_2$.

In further embodiments, the formulation comprises polyvinyl alcohol (PVA). In some embodiments, the PVA is at a concentration ranging from about 1 mg/mL to about 10 mg/mL. In some embodiments, the PVA is at a concentration of about 5 mg/mL. Not being bound by any particular theory, the addition of PVA can associate with key proteins at the surface of adenovirus and prevent detrimental interactions.

In a particular embodiment, the formulation comprises an adenovirus vector, dextran sulfate with an average molecular weight between about 6500 Da and about 10000 Da, dextran sulfate with an average molecular weight between about 500000 Da and about 3000000 Da, a combination of TRIS and benzoate ion as a displaced buffer, EDTA, sucrose, polysorbate 80, and polyvinyl alcohol. The pH of this formulation is about 6.

In another particular embodiment, the formulation comprises an adenovirus vector, a dextran sulfate with an average molecular weight between about 6500 Da and about 10000 Da, a dextran sulfate with an average molecular weight between about 500000 Da and about 3000000 Da, a combination of TRIS and benzoate ion as a displaced buffer, EDTA, sucrose, and polysorbate 80. The pH of this formulation is about 7.

In still another particular embodiment, the formulation comprises an adenovirus vector, a dextran sulfate with an average molecular weight between about 6500 Da and about 10000 Da, a dextran sulfate with an average molecular weight between about 500000 Da and about 3000000 Da, a combination of TRIS and benzoate ion as a displaced buffer, sucrose, and polysorbate 80. The pH of this formulation is about 6.5.

In general, the formulations of the invention maintain high infectivity when stored for at least twelve months, e.g. for twenty-four months at a temperature ranging from 2° C. to 8° C. In some embodiments, the formulations maintain high infectivity when stored for at least twelve months, e.g. for twenty-four months at a temperature of about 4° C. In some embodiments, the formulation maintains high infectivity when stored for three months at a temperature of 25° C. Methods to measure the activity (e.g., infectivity and/or viability) of viruses are routine and conventional. For adenoviruses, for example, one can measure the number of infectious particles with, e.g., cytopathic effect (CPE), end point dilution (EPD), a plaque forming assay, or can use Fluorescence Activated Cell Sorter (FACS) analysis, e.g., in conjunction with FITC labeled anti-penton (coat protein) antibody. Such measurements detect the amount of available (measurable) viral infectivity, e.g., infective virions that are not adsorbed to other virions or to the walls of the container in which they reside.

In some embodiments, the formulation loses less than 2 log infectivity of the starting infectivity when stored for at least twelve months, e.g. for twenty-four months at a temperature ranging from 2° C. to 8° C. or for three months at 25° C. In some embodiments, the formulation loses less than 1 log infectivity of the starting infectivity when stored for at least twelve months, e.g. for twenty-four months at a temperature ranging from 2° C. to 8° C. or for three months at 25° C. In some embodiments, the formulation loses less than 0.5 log infectivity of the starting infectivity when stored for at least twelve months, e.g. for twenty-four months at a temperature ranging from 2° C. to 8° C. or for three months at 25° C. In some embodiments, the log infectivity of the formulation is measured by a FACS assay. In some embodiments, the log infectivity of the formulation is measured by a $TCID_{50}$ assay.

In a preferred embodiment, the formulation is a pharmaceutical formulation. For example, the adenovirus vectors can be combined with one or more pharmaceutically acceptable carriers for an injectable pharmaceutical formulation. The term "carrier," as used herein, refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, allow the constitution of injectable solutions.

The sterile injectable preparations can be a solution or suspension in a nontoxic parenterally acceptable solvent or diluent. Examples of pharmaceutically acceptable carriers are saline, buffered saline, isotonic saline (e.g., monosodium or disodium phosphate, sodium, potassium, calcium or magnesium chloride, or mixtures of such salts), Ringer's solution, dextrose, water, sterile water, glycerol, ethanol, and combinations thereof. 1,3-Butanediol and sterile fixed oils are conveniently employed as solvents or suspending media. Any bland fixed oil can be employed including synthetic mono- or di-glycerides. Fatty acids such as oleic acid also find use in the preparation of injectables.

The pharmaceutical formulation can be introduced parenterally or transmucosally, e.g., orally, nasally, or rectally, or transdermally. In some embodiments, the pharmaceutical formulation is administered parenterally, e.g., via intravenous injection, and also including, but are not limited to, intra-arteriole, intramuscular, intradermal, subcutaneous, intraperitoneal, intraventricular, intravitreal and intracranial administration. In some embodiments, the pharmaceutical formulation is suitable for administration by injection or infusion.

The pharmaceutical formulations of the present invention provide long-term storage stability for adenovirus vector compositions at varying degrees of virus concentration and may be administered to a variety of vertebrate organisms, e.g., mammals and especially humans. The stabilized pharmaceutical formulations of the present invention are preferably recombinant adenovirus-based compositions, wherein administered as a vaccine, for example, may offer a prophylactic advantage to previously uninfected individuals and/or provide a therapeutic effect by reducing viral load levels within an infected individual, thus prolonging the asymptomatic phase of a particular microbial infection, such as an HIV infection.

A particular aspect of the invention is a recombinant adenovirus formulation (i.e., an adenovirus containing a whole or a portion of a transgene which is expressed within the target host subsequent to host administration, such as in any mammalian/human gene therapy- or gene vaccination-based methodology available to the skilled artisan) which shows enhanced stability characteristics described herein with a virus concentration in the range from about $1\times10^7$ vp/mL to about $1\times10^{13}$ vp/mL, from about $1\times10^7$ vp/mL to about $1\times10^{12}$ vp/mL, or from about $1\times10^7$ vp/mL to about $1\times10^{10}$ vp/mL. Therapeutic, prophylactic or diagnostic compositions of the formulations of the present invention are administered to an individual in amounts sufficient to treat, prevent or diagnose the respective disorder. The effective amount for human administration may vary according to a variety of factors such as the individual's condition, weight, sex and age. Other factors include the mode of administration. The amount of expressible DNA to be administered to a human recipient will depend on the strength of the transcriptional and translational promoters used in the recombinant viral construct, and, if used as a vaccine, on the immunogenicity of the expressed gene product, as well as the level of pre-existing immunity to a virus such as adenovirus.

In some embodiments, the pharmaceutical formulation is used in gene therapy. In some embodiments, the pharmaceutical formulation is used in cancer gene therapy. In some embodiments, for gene therapy of a cancer, the pharmaceutical formulation is administered by injection into a tumor or into tissues surrounding the tumor. In a particular embodiment, the pharmaceutical formulation is administered by direct injection into the tumor.

Methods for the Preparation of a Storage Stable Aqueous Formulation

The present invention is also directed to a method for the preparation of a storage stable aqueous formulation, comprising: forming a mixture of an adenovirus vector and at least one anionic polymer.

In some embodiments, the adenovirus is a human adenovirus. In some embodiments, the human adenovirus is a serotype from a subgroup which shows negligible or no tumor growth in animals, such as subgroup C (Ad1, Ad2, Ad5 and Ad6), subgroup D (Ad8, Ad9, Ad10, Ad13, Ad15, Ad17, Ad19, Ad20, Ad22, Ad23, Ad24, Ad25, Ad26, Ad27, Ad28, Ad29, Ad30, Ad32, Ad33, Ad36, Ad37, Ad38, Ad39, Ad42, Ad43, Ad44, Ad45, Ad46, and Ad4), subgroup B (Ad3, Ad7, Ad11, Ad14, Ad16, Ad21, Ad34, and Ad35) and subgroup E (Ad4). For an exhaustive adenovirus classification scheme, see *Fundamental Virology*, 3$^{rd}$ Edition, Chapter 30, page 980, Ed. Fields, et al. 1996, Lippincott-Raven. In some embodiments, the serotype is Ad5 or Ad35 as a single vector, maintaining a concentration in an aqueous solution in the range from about $1\times10^7$ to about $1\times10^{13}$ vp/ml (virus particles/milliliter), from about $1\times10^7$ vp/mL to about $1\times10^{12}$ vp/mL, or from about $1\times10^7$ vp/mL to about $1\times10^{10}$ vp/mL.

Examples of suitable anionic polymers include, but are not limited to, dextran sulfate, keratan sulfate, heparin, salts of hyaluronic acid, salts of colominic acid, chondroitin sulfate, carrageenan, glucomannan, salts of carboxymethyl cellulose, salts of alginic acid, salts of pectinic acid, salts of pectic acid, agar, carboxylic acid salts of polysaccharides, polyglutamate, polyasparate, salts of poly(galacturonic acid), salts of acrylic acid polymers and copolymers, salts of methacrylic acid polymers and copolymers, poly(vinyl sulfate), as well as fragments or derivatives thereof. Examples of suitable salts associated with anionic polymers include, but are not limited to, sodium, potassium, calcium, zinc, magnesium or ammonium salts, or organic counter ions including substituted ammonium or guanidinium ions.

In some embodiments, the at least one anionic polymer is selected from the group consisting of dextran sulfates, carboxymethyl cellulose, polyglutamate, polyaspartate, and salt forms thereof, for example sodium salts. In some embodiments, the at least one anionic polymer is at a concentration ranging from about 0.5 mg/mL to about 10 mg/mL.

In some embodiments, the at least one anionic polymer is dextran sulfate. In some embodiments, the dextran sulfate has an average molecular weight between about 3000 Daltons ("Da") and about 3000000 Da. In some embodiments, the dextran sulfate has an average molecular weight between about 6500 Da and about 10000 Da. In some embodiments, the dextran sulfate with an average molecular weight between about 6500 Da and about 10000 Da is at a concentration ranging from about 4 mg/mL to about 6 mg/mL. In some embodiments, the dextran sulfate has an average molecular weight between about 500000 Da and about 3000000 Da. In some embodiments, the dextran sulfate with an average molecular weight between about 500000 Da and about 3000000 Da is at a concentration ranging from 0.9 mg/mL to about 6 mg/mL. In some embodiments, the dextran sulfate is selected from the group consisting of dextran sulfate having an average molecular weight of about 5000 Da, dextran sulfate having an average molecular weight between about 6500 Da and about 10000 Da, dextran sulfate having an average molecular weight between about 9000 Da and about 20000 Da, and dextran sulfate having an average molecular weight between about 500000 Da and about 3000000 Da.

In some embodiments, the mixture comprises one anionic polymer. In some embodiments, the mixture comprises a combination of anionic polymers. For example, a combination of dextran sulfate of different molecular weights can be used. In some embodiments, the solution comprises one dextran sulfate with an average molecular weight between about 6500 Da and about 10000 Da and one dextran sulfate has an average molecular weight between about 500000 Da and about 2000000 Da.

In some embodiments, the at least one anionic polymer is sodium carboxymethyl cellulose. In some embodiments, the sodium carboxymethyl cellulose has an average molecular weight between about 20000 Da and 1000000 Da, between about 50000 Da and 800000 Da, or between 90000 Da and 700000 Da. In some embodiments, the sodium carboxymethyl cellulose has an average molecular weight of about 90000 Da.

In some embodiments, the mixture also comprises at least one buffer. The buffer can be either a conventional buffer or a displaced buffer. A typical aqueous adenovirus solution is formulated in a conventional buffer. Examples of a conventional buffer include, but are not limited to, phosphate, citrate, histidine, succinate, acetate, and glycine. In some embodiments, the at least one buffer is a displaced buffer having an ionizable group with a pKa value at least one unit higher or lower than the pH of the formulation and having no ionizable group with a pKa value within one unit of the pH of the formulation.

Examples of compounds that can be usefully incorporated in the solution as additives and that may, subject to the pH of the formulation, function as displaced buffers are known and include, but are not limited to, histidine, maleate, sulphite, cyclamate, hydrogen sulphate, serine, arginine, lysine, asparagine, methionine, threonine, tyrosine, isoleucine, valine, leucine, alanine, glycine, tryptophan, gentisate, salicylate, glyoxylate, aspartame, glucuronate, aspartate, glutamate, tartrate, gluconate, lactate, glycolic acid, adenine, succinate, ascorbate, benzoate, phenylacetate, gallate, cytosine, p-aminobenzoic acid, sorbate, acetate, propionate, alginate, urate, 2-(N-morpholino)ethanesulphonic acid, bicarbonate, bis(2-hydroxyethyl)iminotris(hydroxymethyl) methane, N-(2-acetamido)-2, iminodiacetic acid, 2-[(2-amino-2-oxoethyl)amino]ethanesulphonic acid, piperazine, N,N'-bis(2-ethanesulphonic acid), phosphate, N,N-bis(2-hydroxyethyl)-2, aminoethanesulphonic acid, 3-[N,N-bis(2-hydroxyethyl)amino]-2, hydroxypropanesulphonic acid, triethanolamine, piperazine-N,N'-bis(2, hydroxypropanesulphonic acid), tris(hydroxymethyl)aminomethane, N-tris(hydroxymethyl)glycine, N-tris(hydroxymethyl)methyl-3-aminopropanesulphonic acid, ammonium ion, borate, 2-(N-cyclohexylamino)ethanesulphonic acid, 2-amino-2-methyl-1-propanol, palmitate, creatine, creatinine, and salts thereof. The particular choice of the compound will depend on pH of the formulation.

In some embodiments, the buffer is selected from the group consisting of TRIS, benzoate ion, and a combination thereof. Benzoic acid or its salts, such as sodium or potassium slat, can be used as the source of benzoate ion. Either TRIS base or TRIS hydrochloride can be used as a source of TRIS. In some embodiments, the buffer comprises TRIS and benzoate ion. The concentration of each buffer is usually in the range between about 1 mM and 100 mM, between about 5 mM and about 50 mM, or between about 5 mM and about 20 mM.

In some embodiments, the pH of the formulation is between 5 and 8. In some embodiments, the pH of the formulation is between 5.5 and 7.5. In some embodiments, the pH of the formulation is between 6 and 7.

In some embodiments, the mixture also comprises a tonicity modifier. A purpose of inclusion of a tonicity modifier in the formulation is to attain the desired ionic strength or osmolarity. Examples of the tonicity modifier include, but are not limited to, an inorganic salt, an amino acid, and a sugar or sugar alcohol. In some embodiments, the tonicity modifier is an inorganic salt which is a combination of sodium, potassium, calcium, or ammonium, with chloride, sulfate nitrate, lactate, succinate, acetate, maleate, or lactate. In some embodiments, the tonicity modifier is an amino acid selected from the group consisting of histidine, glycine, arginine, and methionine. In some embodiments, the tonicity modifier is a sugar or sugar alcohol selected from the group consisting of 1,2-propanediol, glycerol, mannitol, sorbitol, sucrose, lactose, maltose, and trehalose. In some embodiments, the tonicity modifier is sucrose.

The aqueous formulations of the present invention cover a wide range of osmolarity, including hypotonic, isotonic, and hypertonic formulations. In some embodiments, the formulation is substantially isotonic. In some embodiments, the tonicity modifier is at a concentration sufficient to provide osmolarity between about 100 mOsm/l and about 1000 mOsm/l. In some embodiments, the tonicity modifier is at a concentration sufficient to provide osmolarity between about 200 mOsm/l and about 500 mOsm/l. In some embodiments, the tonicity modifier is at a concentration sufficient to provide osmolarity between about 250 mOsm/l and about 350 mOsm/l. In some embodiments, the formulation is intended for administration to a subject by intramuscular or subcutaneous injection, and the osmolarity of the formulation is selected to minimize pain upon injection. Contributions to ionic strength or osmolarity may come from ions produced by the buffering compound as well as from the ions of non-buffering salts.

In some embodiments, the mixture further comprises a surfactant. In some embodiments, the surfactant is a non-ionic surfactant. In some embodiments, the non-ionic surfactant is selected from the group consisting of polysorbates and poloxamers. Examples of polysorbates include, but are not limited to, polysorbate 20, polysorbate 40, polysorbate 60, and polysorbate 80. Examples of poloxamers include, but are not limited to, poloxamer 182, poloxamer 188, poloxamer 331, poloxamer 338, and poloxamer 407. In some embodiments, the non-ionic surfactant is polysorbate 80. In some embodiments, the polysorbate 80 is at a concentration ranging from about 0.05 mg/mL to about 0.6 mg/mL. Not being bound by any particular theory, the addition of the non-ionic surfactant can decrease the surface tension of the aqueous formulation, reduce absorption to container surfaces and increase the adenovirus stability.

In some embodiments, the mixture also comprises ethylenediaminetetraacetic acid anion (EDTA). In some embodiments, EDTA is at a concentration of less than about 5 mM. In some embodiments, EDTA is at a concentration of less than about 1 mM. In some embodiments, EDTA is at a concentration ranging from about 0.05 mM to about 0.5 mM.

In further embodiments, the mixture also comprises at least one salt of a divalent cation. In some embodiments, the at least one salt of a divalent cation is selected from the group consisting of $MgCl_2$, $MgSO_4$, $CaCl_2$, $CaSO_4$, $ZnCl_2$, $ZnSO_4$, $MnCl_2$, and $MnSO_4$. In some embodiments, the at least one salt of a divalent cation is at a concentration ranging from about 0.5 mM to about 5 mM. In some embodiments, the at least one salt of a divalent cation is at a concentration of about 1.5 mM. In some embodiments, the at least one salt of a divalent cation is $MgCl_2$.

In some embodiments, the mixture also comprises polyvinyl alcohol (PVA). In some embodiments, the PVA is at a concentration ranging from about 1 mg/mL to about 10 mg/mL. In some embodiments, the PVA is at a concentration of about 5 mg/mL. Not being bound by any particular theory, the addition of PVA can associate with key proteins at the surface of adenovirus and prevent detrimental interactions.

In a particular embodiment, the storage stable adenovirus aqueous formulation comprises an adenovirus vector, a dextran sulfate with an average molecular weight between about 6500 Da and about 10000 Da, a dextran sulfate with an average molecular weight between about 500000 Da and about 3000000 Da, a combination of TRIS and benzoate ion as a displaced buffer, EDTA, sucrose, polysorbate 80, and polyvinyl alcohol. The pH of this formulation is about 6.

In another particular embodiment, the storage stable adenovirus aqueous formulation comprises an adenovirus vector, a dextran sulfate with an average molecular weight between about 6500 Da and about 10000 Da, a dextran sulfate with an average molecular weight between about 500000 Da and about 3000000 Da, a combination of TRIS and benzoate ion as a displaced buffer, EDTA, sucrose, and polysorbate 80. The pH of this formulation is about 7.

In still another particular embodiment, the storage stable adenovirus aqueous formulation comprises an adenovirus vector, a dextran sulfate with an average molecular weight between about 6500 Da and about 10000 Da, a dextran sulfate with an average molecular weight between about 500000 Da and about 3000000 Da, a combination of TRIS and benzoate ion as a displaced buffer, sucrose, and polysorbate 80. The pH of this formulation is about 6.5.

In some embodiments, the storage stable adenovirus aqueous formulation maintains high infectivity when stored for twenty-four months at a temperature ranging from 2° C. to 8° C. In some embodiments, the storage stable adenovirus aqueous formulation maintains high infectivity when stored for twenty-four months at a temperature of about 4° C. In some embodiments, the storage stable adenovirus aqueous formulation maintains high infectivity when stored for three months at a temperature of 25° C. Methods to measure the activity (e.g., infectivity and/or viability) of viruses are routine and conventional. For adenoviruses, for example, one can measure the number of infectious particles with, e.g., cytopathic effect (CPE), end point dilution (EPD), a plaque forming assay, or can use Fluorescence Activated Cell Sorter (FACS) analysis, e.g., in conjunction with FITC labeled anti-penton (coat protein) antibody. Such measurements detect the amount of available (measurable) viral infectivity, e.g., infective virions that are not adsorbed to other virions or to the walls of the container in which they reside.

In some embodiments, the storage stable adenovirus aqueous formulation loses less than 2 log infectivity of the starting infectivity when stored for at least twelve months, e.g. for twenty-four months at a temperature ranging from 2° C. to 8° C. or for three months at 25° C. In some embodiments, the storage stable adenovirus aqueous formulation loses less than 1 log infectivity of the starting infectivity when stored for at least twelve months, e.g. for twenty-four months at a temperature ranging from 2° C. to 8° C. or for three months at 25° C. In some embodiments, the storage stable adenovirus aqueous formulation loses less than 0.5 log infectivity of the starting infectivity when stored for at least twelve months, e.g. for twenty-four months at a temperature ranging from 2° C. to 8° C. or for three months at 25° C. In some embodiments, the log infectivity of the formulation is measured by a FACS assay. In some embodiments, the log infectivity of the formulation is measured by a $TCID_{50}$ assay.

In some embodiments, the storage stable adenovirus aqueous formulation is a pharmaceutical formulation. For example, the adenovirus vectors can be combined with one or more pharmaceutically acceptable carriers for an injectable pharmaceutical formulation. In some embodiments, the pharmaceutical formulation is suitable for administration by injection or infusion.

The invention is further illustrated by the following non-limiting examples.

EXAMPLES $TCID_{50}$ Adenovirus Infectivity Assay

The $TCID_{50}$ (Tissue Culture Infectious Dose 50) assay is a method for titrating the infectivity of adenovirus, using a $TCID_{50}$ end-point dilution method in a 96-well format.

96 well plates were seeded at $1 \times 10^5$ Human Embryonic Kidney (HEK) 293 cells/mL 1 day prior to infection with adenovirus samples. The adenovirus samples were removed from storage and serially diluted from $10^{-1}$ to $10^{-12}$ in Dulbecco's Modified Eagle Media (DMEM)+2% fetal bovine serum (FBS)+4 mM glutamine (Gln). Each dilution was used to infect 8 wells on a 96 well plate (100 μL/well). One column of wells per plate had fresh DMEM+2% FBS+4 mM Gln added to it (100 μL/well), to act as a negative control. The plates were moved to the 37° C. incubator and will be screened for cytopathic effects (CPE) after 7-10 days.

Example 1—Effect of pH

Figure 1:
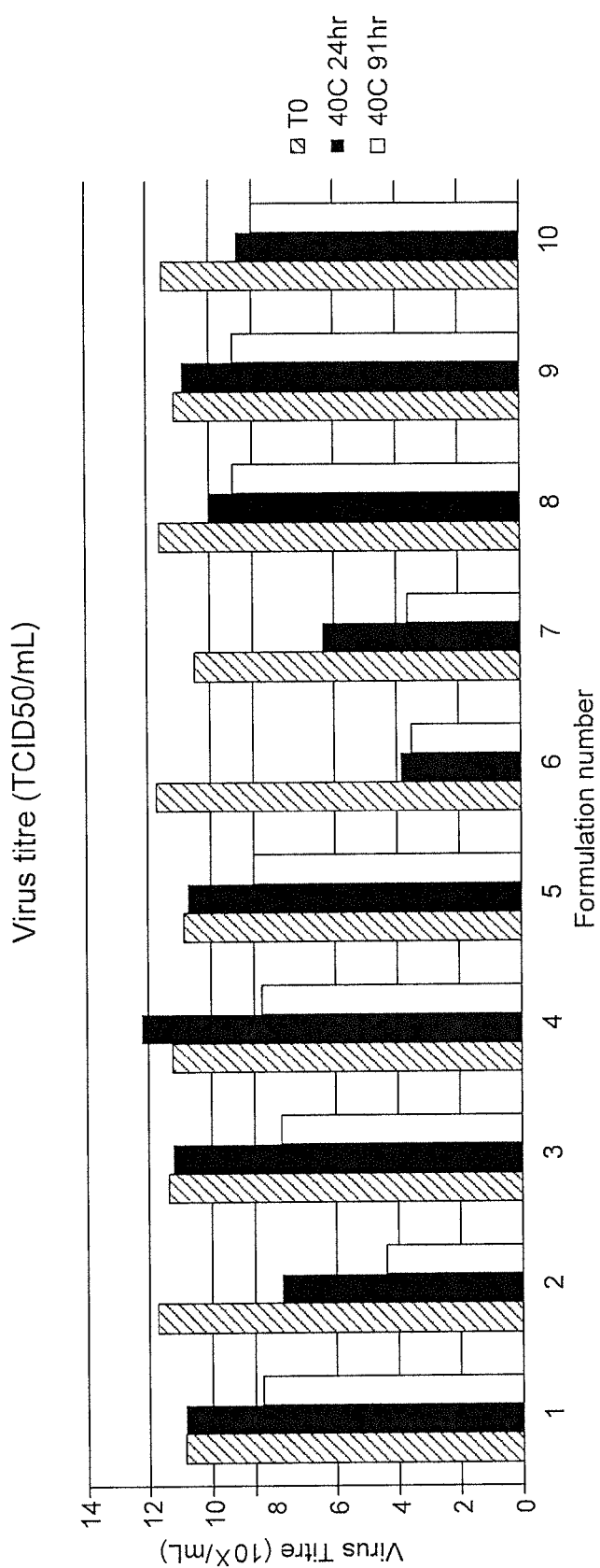
FIG. 1 shows the effect of pH on the stability of adenovirus formulations.

The effect of pH on the stability of adenovirus was examined with two sets of formulations with five different pH values (Table 1). Formulations 1-5 were formulated with NaCl as the tonicity modifier whereas 1,2-propandiol was used for Formulations 6-10. The $TCID_{50}$ assay was used to titrate the infectivity of the formulations at T0 (start), 24 hr at 40° C. storage, and 91 hr at 40° C. storage. FIG. 1 indicates that the stability of the adenovirus formulation is better when formulated at pH from 6-8.

TABLE 1

| FORMULATION NUMBER | Citrate (mM) | Phosphate (mM) | NaCl (mM) | 1,2-propanediol (mM) | pH |
|---|---|---|---|---|---|
| 1 | 5 | 5 | 150 | | 4 |
| 2 | 5 | 5 | 150 | | 5 |
| 3 | 5 | 5 | 150 | | 6 |
| 4 | 5 | 5 | 150 | | 7 |
| 5 | 5 | 5 | 150 | | 8 |
| 6 | 5 | 5 | | 300 | 4 |

TABLE 1-continued

| FORMULATION NUMBER | Citrate (mM) | Phosphate (mM) | NaCl (mM) | 1,2-propanediol (mM) | pH |
|---|---|---|---|---|---|
| 7 | 5 | 5 | | 300 | 5 |
| 8 | 5 | 5 | | 300 | 6 |
| 9 | 5 | 5 | | 300 | 7 |
| 10 | 5 | 5 | | 300 | 8 |

Example 2—Effect of Ionic Strength

Figure 2:
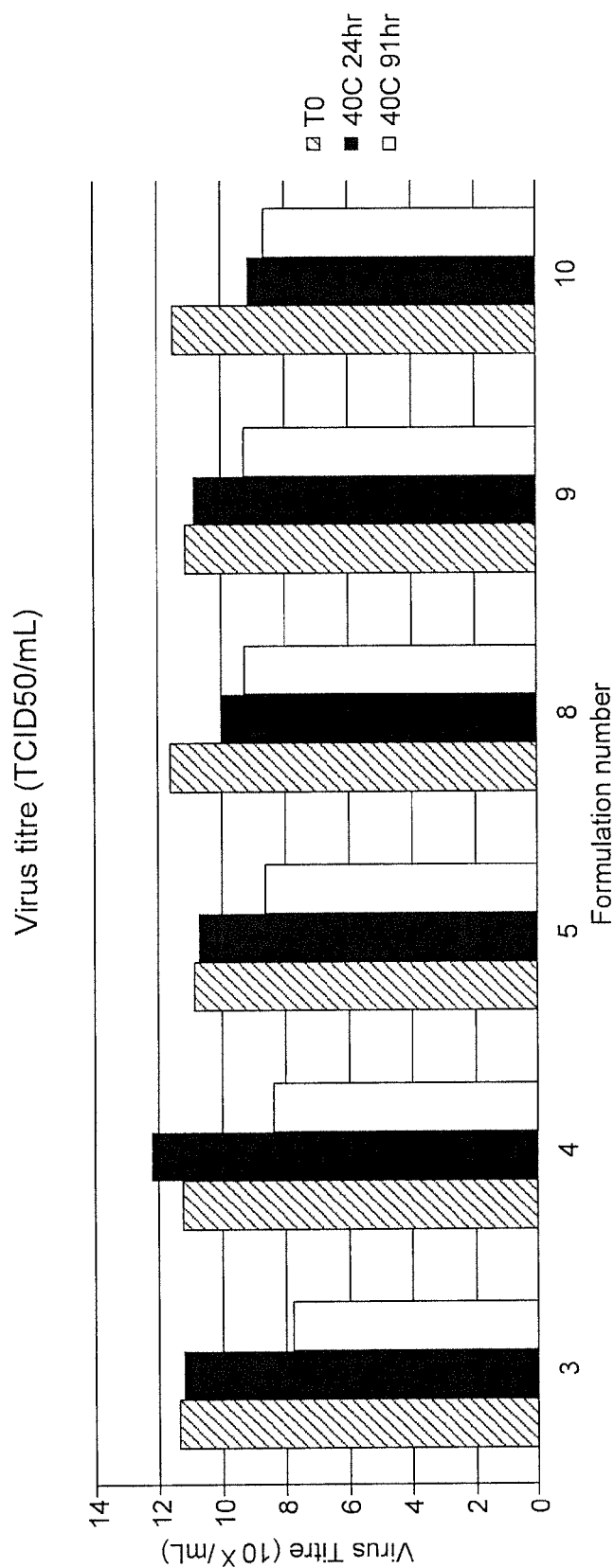
FIG. 2 shows the effect of ionic strength on the stability of adenovirus formulations.

The effect of ionic strength on the stability of adenovirus was examined with two sets of formulations with two different tonicity modifiers (Table 2). Formulations 3-5 were formulated with NaCl as the tonicity modifier whereas 1,2-propandiol was used for Formulations 8-10. The $TCID_{50}$ assay was used to titrate the infectivity of the formulations at T0 (start), 24 hr at 40° C. storage, and 91 hr at 40° C. storage. FIG. 2 indicates that the formulations of low ionic strength (with 300 mM 1,2-propanediol) have a better stabilizing effect than the formulations of high ionic strength (with 150 mM sodium chloride).

TABLE 2

| FORMULATION NUMBER | Citrate (mM) | Phosphate (mM) | NaCl (mM) | 1,2-propanediol (mM) | pH |
|---|---|---|---|---|---|
| 3 | 5 | 5 | 150 | | 6 |
| 4 | 5 | 5 | 150 | | 7 |
| 5 | 5 | 5 | 150 | | 8 |
| 8 | 5 | 5 | | 300 | 6 |
| 9 | 5 | 5 | | 300 | 7 |
| 10 | 5 | 5 | | 300 | 8 |

Example 3—Effect of Conventional and Displaced Buffers

Figure 3:
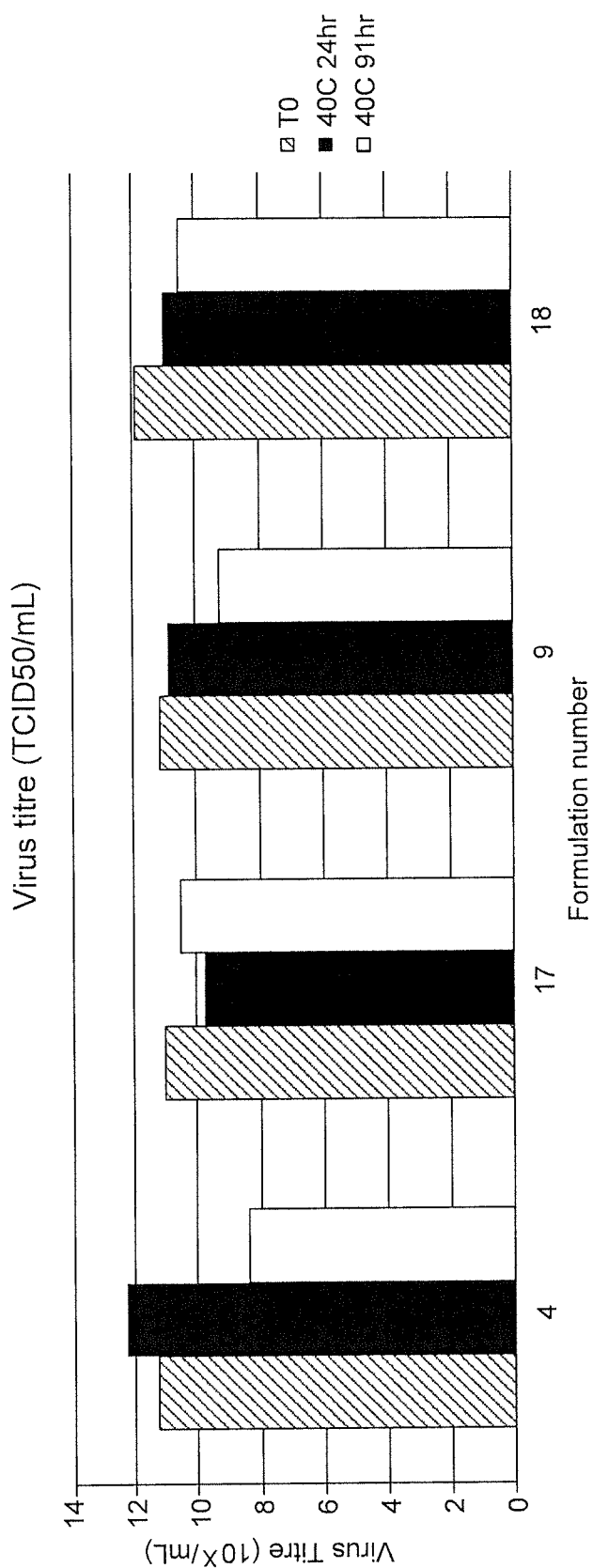
FIG. 3 shows the effect of conventional and displaced buffers on the stability of adenovirus formulations.

The effect of conventional and displaced buffers on the stability of adenovirus was examined with two sets of formulations with two different buffering systems (Table 3). Formulations 4 and 9 were formulated with conventional buffers, citrate and phosphate; whereas Formulations 17 and 18 were formulated with a displaced buffer system, a combination of TRIS and benzoate. The $TCID_{50}$ assay was used to titrate the infectivity of the formulations at T0 (start), 24 hr at 40° C. storage, and 91 hr at 40° C. storage. FIG. 3 indicates that the stability of adenovirus formulations increases in the displaced buffer (a combination of TRIS and benzoate).

TABLE 3

| FORMULATION NUMBER | Citrate (mM) | Phosphate (mM) | TRIS (mM) | NaCl (mM) | 1,2-propanediol (mM) | Benzoate (mM) | pH |
|---|---|---|---|---|---|---|---|
| 4 | 5 | 5 | | 150 | | | 7 |
| 9 | 5 | 5 | | | 300 | | 7 |
| 17 | | | 10 | 150 | | 10 | 7 |
| 18 | | | 10 | | 300 | 10 | 7 |

Example 4—Effect of Addition of EDTA

Figure 4:
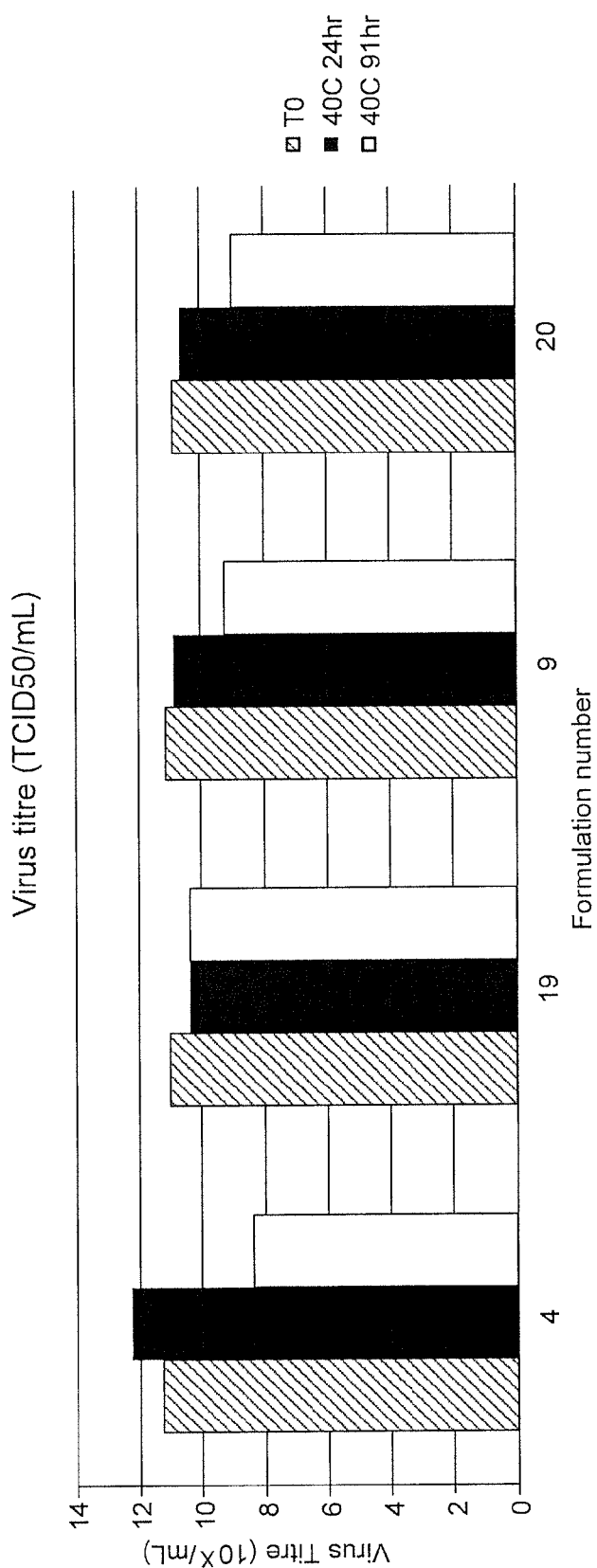
FIG. 4 shows the effect of addition of EDTA on the stability of adenovirus formulations.

The effect of addition of EDTA on the stability of adenovirus was examined with two sets of formulations with two different tonicity modifiers (Table 4). Formulations 4 and 19 were formulated with NaCl; whereas Formulations 9 and 20 were formulated with 1,2-propandiol. The $TCID_{50}$ assay was used to titrate the infectivity of the formulations at T0 (start), 24 hr at 40° C. storage, and 91 hr at 40° C. storage. FIG. 4 indicates that the stability of adenovirus formulations with sodium chloride increases with the addition of EDTA.

TABLE 4

| FORMULATION NUMBER | Citrate (mM) | Phosphate (mM) | NaCl (mM) | 1,2-propanediol (mM) | EDTA (mM) | pH |
|---|---|---|---|---|---|---|
| 4 | 5 | 5 | 150 | | | 7 |
| 9 | 5 | 5 | | 300 | | 7 |
| 19 | 5 | 5 | 150 | | 1 | 7 |
| 20 | 5 | 5 | | 300 | 1 | 7 |

Example 5—Effect of Addition of Polyethylenimine (PEI)

Figure 5:
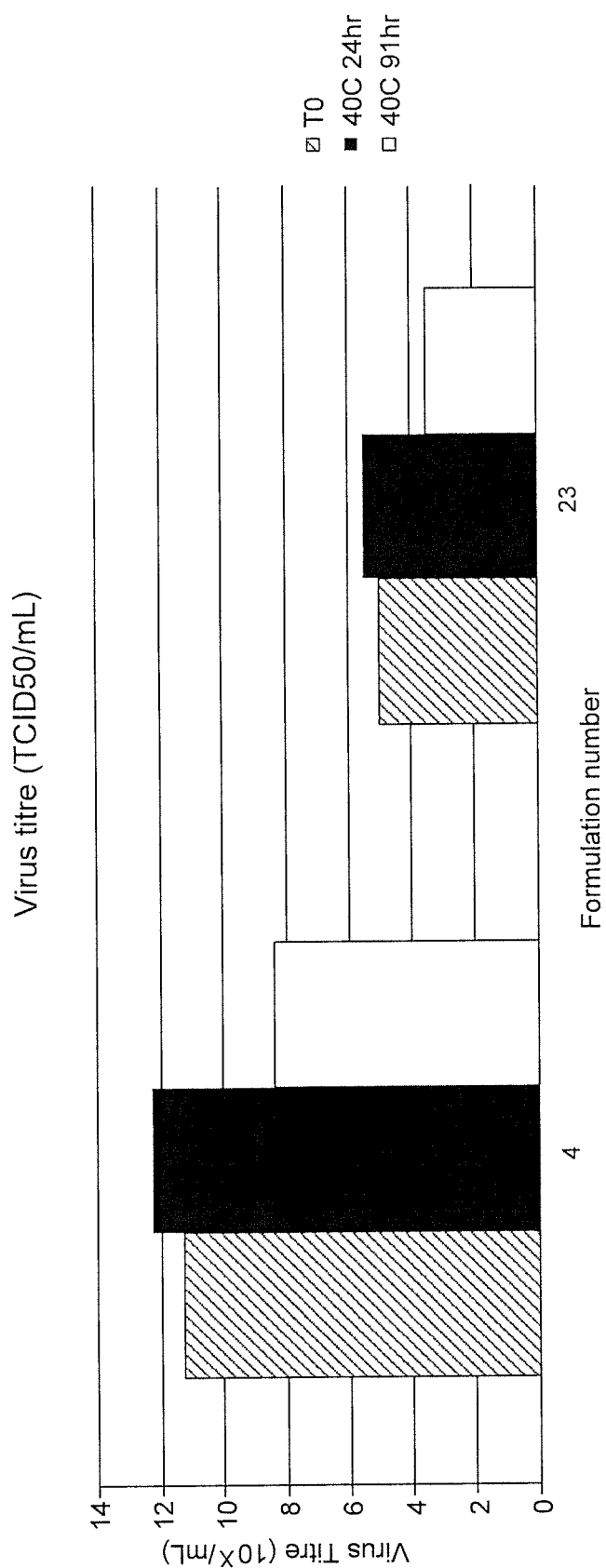
FIG. 5 shows the effect of addition of polyethylenimine (PEI) on the stability of adenovirus formulations.

The effect of addition of a cationic polymer, PEI with average Mn~1,800, on the stability of adenovirus was examined with Formulations 4 and 23 (Table 5). Formulation 23 was formulated with an additional 5 mg/mL PEI, a cationic polymer. The $TCID_{50}$ assay was used to titrate the infectivity of the formulations at T0 (start), 24 hr at 40° C. storage, and 91 hr at 40° C. storage. FIG. 5 indicates that the addition of PEI with average $M_n$~1,800 decreases the stability of adenovirus formulations.

TABLE 5

| FORMULATION NUMBER | Citrate (mM) | Phosphate (mM) | NaCl (mM) | PEI (mg/ml) | pH |
|---|---|---|---|---|---|
| 4 | 5 | 5 | 150 | | 7 |
| 23 | 5 | 5 | 150 | 5 | 7 |

Example 6—Effect of Addition of Sodium Carboxymethyl Cellulose (CMC)

Figure 6A:
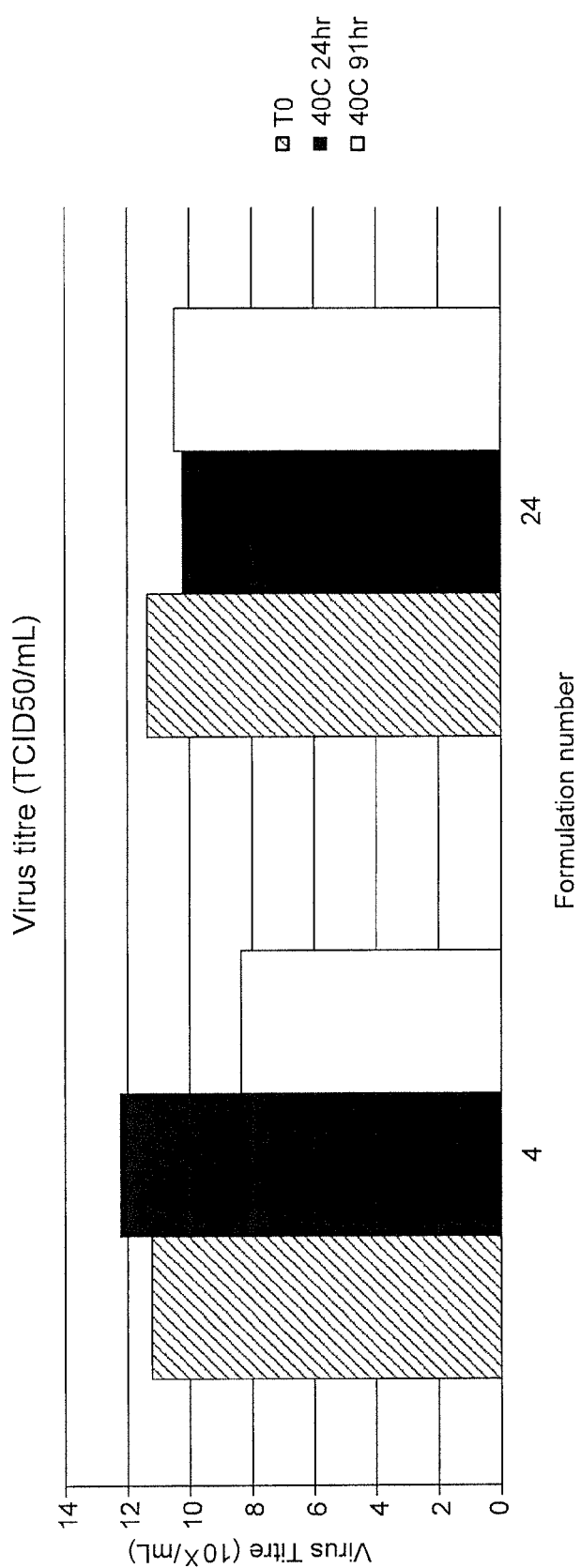
FIGS. 6A and 6B show the effect of addition of sodium carboxymethyl cellulose on the stability of adenovirus formulations.
Figure 6B:
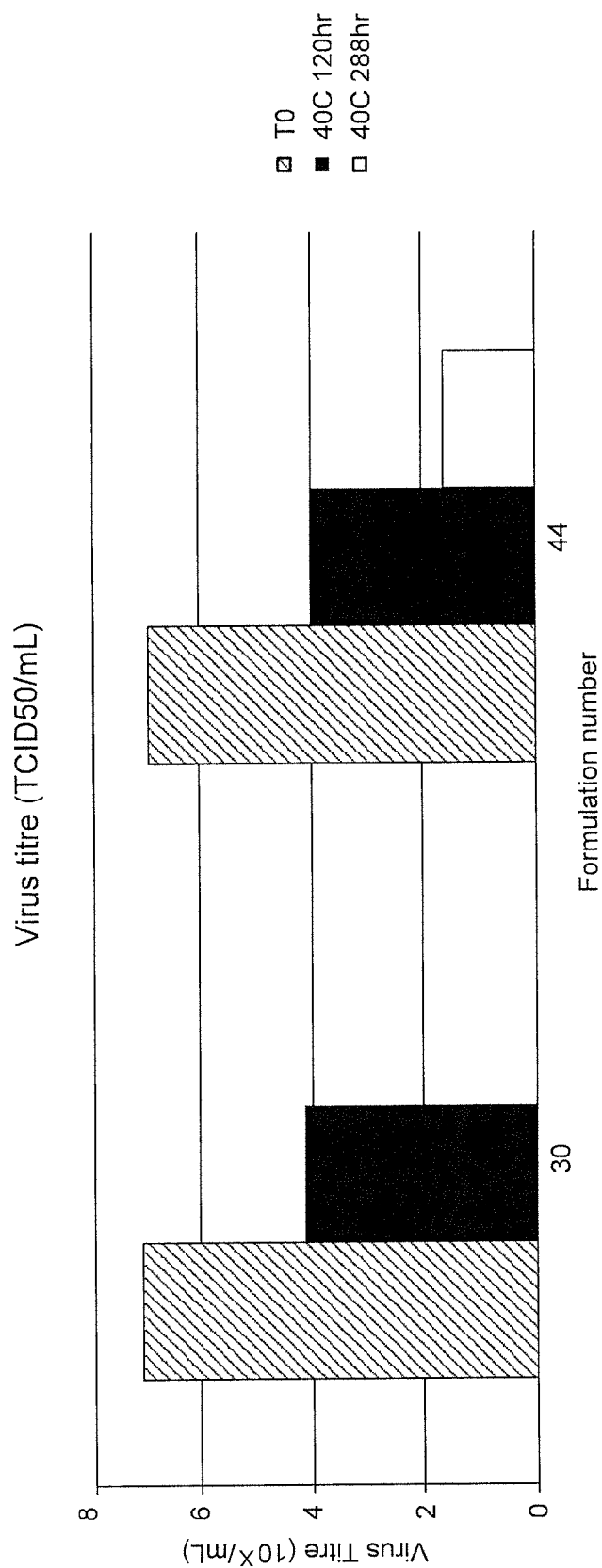

The effect of addition of CMC on the stability of adenovirus was examined with two experiments (Table 6). In the first experiment, Formulations 4 and 24 were compared, where Formulation 24 was formulation with an additional 5 mg/mL CMC, an anionic polymer. The $TCID_{50}$ assay was used to titrate the infectivity of the formulations at T0 (start), 24 hr at 40° C. storage, and 91 hr at 40° C. storage. FIG. 6A indicates that the addition of CMC increases the stability of adenovirus formulations. In the second experiment, Formulations 30 and 44 were compared, where Formulation 44 was formulation with an additional 5 mg/mL CMC. The $TCID_{50}$ assay was used to titrate the infectivity of the formulations at T0 (start), 120 hr at 40° C. storage, and 288 hr at 40° C. storage. FIG. 6B indicates that the addition of CMC increases the stability of adenovirus formulations; as indicated no virus titre was detected in Formulation 30 at the 288 hr time point.

TABLE 6

| FORMULATION NUMBER | Citrate (mM) | Phosphate (mM) | TRIS (mM) | NaCl (mM) | Benzoate (mM) | EDTA (mM) | CMC (mg/mL) | pH |
|---|---|---|---|---|---|---|---|---|
| 4 | 5 | 5 | | 150 | | | | 7 |
| 24 | 5 | 5 | | 150 | | | 5 | 7 |
| 30 | | | 10 | 150 | 10 | 1 | | 7 |
| 44 | | | 10 | 150 | 10 | 1 | 5 | 7 |

Example 7—Effect of Addition of Metal Divalent Ions

Figure 7:
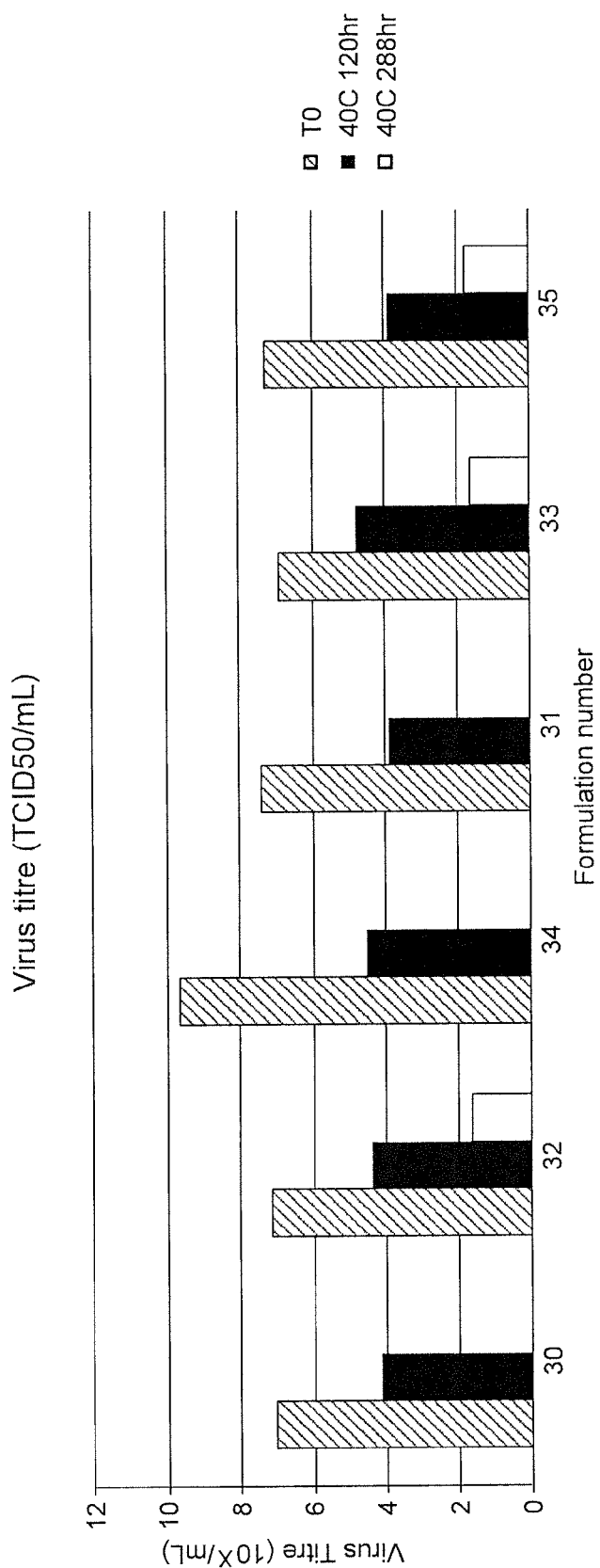
FIG. 7 shows the effect of addition of metal divalent ions on the stability of adenovirus formulations.

The effect of addition of metal divalent ions (e.g., $Ca^{2+}$ or $Mg^{2+}$) on the stability of adenovirus was examined with Formulations 30-35 (Table 7). Formulations 32 and 33 were formulated with $MgCl_2$; whereas Formulations 34 and 35 were formulated with $CaCl_2$. The $TCID_{50}$ assay was used to titrate the infectivity of the formulations at T0 (start), 120 hr at 40° C. storage, and 288 hr at 40° C. storage. FIG. 7 indicates that the addition of $MgCl_2$ and $CaCl_2$ both have a positive effect on the stability of adenovirus formulations.

TABLE 7

| FORMULATION NUMBER | TRIS (mM) | NaCl (mM) | Sodium sulphate (mM) | MgCl2 (mM) | CaCl2 (mM) | Benzoate (mM) | EDTA (mM) | pH |
|---|---|---|---|---|---|---|---|---|
| 30 | 10 | 150 | | | | 10 | 1 | 7 |
| 31 | 10 | | 150 | | | 10 | 1 | 7 |
| 32 | 10 | 150 | | 5 | | 10 | 1 | 7 |
| 33 | 10 | | 150 | 5 | | 10 | 1 | 7 |
| 34 | 10 | 150 | | | 5 | 10 | 1 | 7 |
| 35 | 10 | | 150 | | 5 | 10 | 1 | 7 |

Example 8—Effect of Addition of Polysorbate 80

Figure 8:
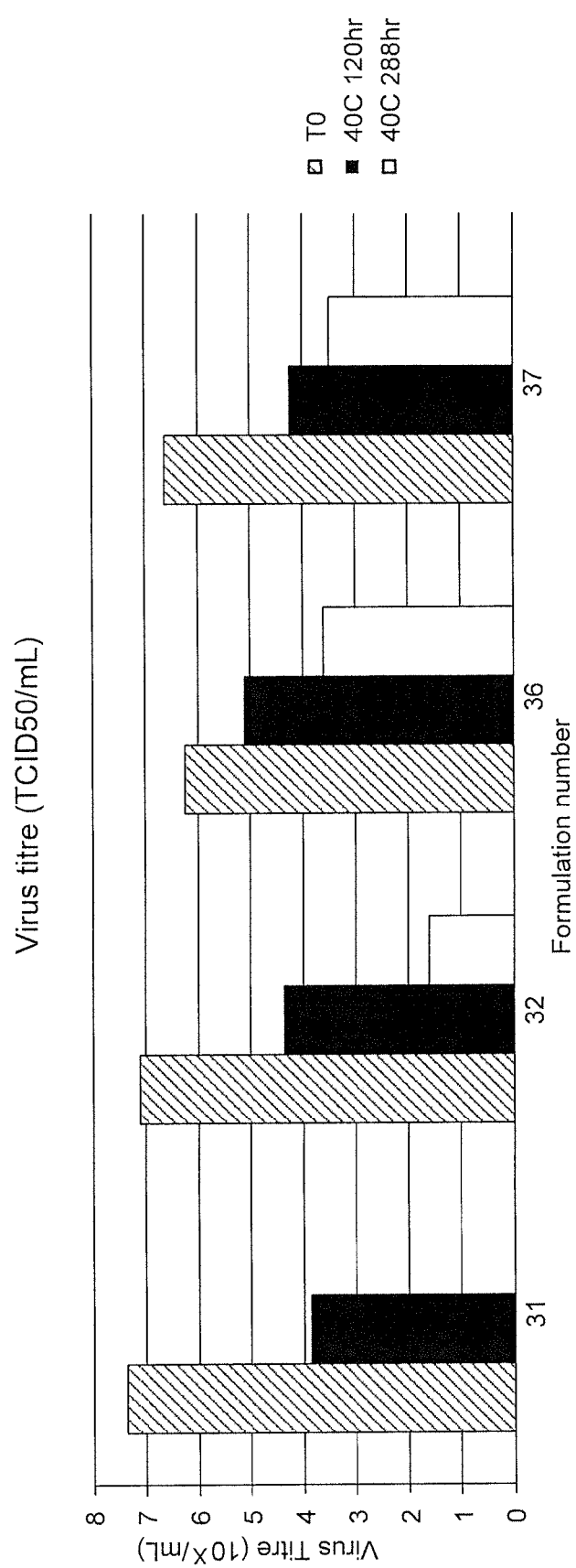
FIG. 8 shows the effect of addition of polysorbate 80 on the stability of adenovirus formulations.

The effect of addition of polysorbate 80, a non-ionic surfactant, on the stability of adenovirus was examined with Formulations 31, 32, 36, and 37 (Table 8). Formulations 36 and 37 were formulated with 0.2 mg/mL polysorbate 80 (Tween 80). The $TCID_{50}$ assay was used to titrate the infectivity of the formulations at T0 (start), 120 hr at 40° C. storage, and 288 hr at 40° C. storage. FIG. 8 indicates that the addition of polysorbate 80 has a positive effect on the stability of adenovirus formulations.

TABLE 8

| FORMULATION NUMBER | TRIS (mM) | NaCl (mM) | Sodium sulphate (mM) | MgCl2 (mM) | Benzoate (mM) | EDTA (mM) | Tween80 (mg/mL) | pH |
|---|---|---|---|---|---|---|---|---|
| 31 | 10 | | 150 | | 10 | 1 | | 7 |
| 32 | 10 | 150 | | 5 | 10 | 1 | | 7 |
| 36 | 10 | 150 | | | 10 | 1 | 0.2 | 7 |
| 37 | 10 | | 150 | | 10 | 1 | 0.2 | 7 |

FACS Adenovirus Infectivity Assay

Several Formulations were analyzed by the FACS (Fluorescence Activated Cell Sorter) assay to determine the number of virus particles per mL, i.e., the virus titre/mL.

The tissue culture plates were purchased from Thermo Fisher and the CD80 antibody was purchased from Pierce. Human Embryonic Kidney (HEK) 293 cells are seeded in DMEM+10% FBS+4 mM Gln 1-2 days prior to being infected with a dilution of one of the Adenovirus vectors. After 17-20 hours the cells were fixed in formalin (Ad5GFP expressing) or incubated with anti-CD80 FITC (Ad5CD80) for 30-60 minutes prior to being fixed in formalin. The samples were then run on the FACS and the % of infected cells was used to determine the number of virus particles per mL, i.e., the virus titre/mL.

Example 9—Effect of Addition of Dextran Sulfate Addition

Figure 9A:
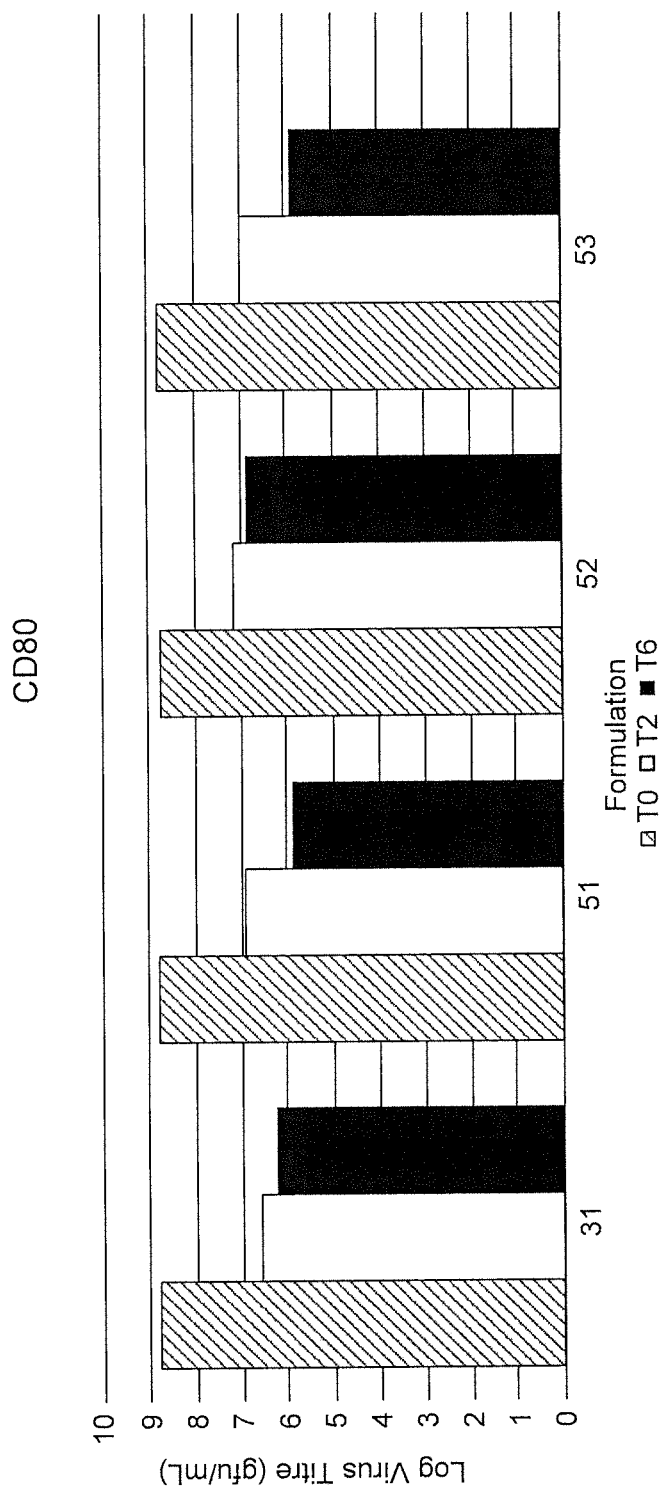
FIGS. 9A and 9B show the effect of addition of dextran sulfate on the stability of adenovirus formulations.
Figure 9B:
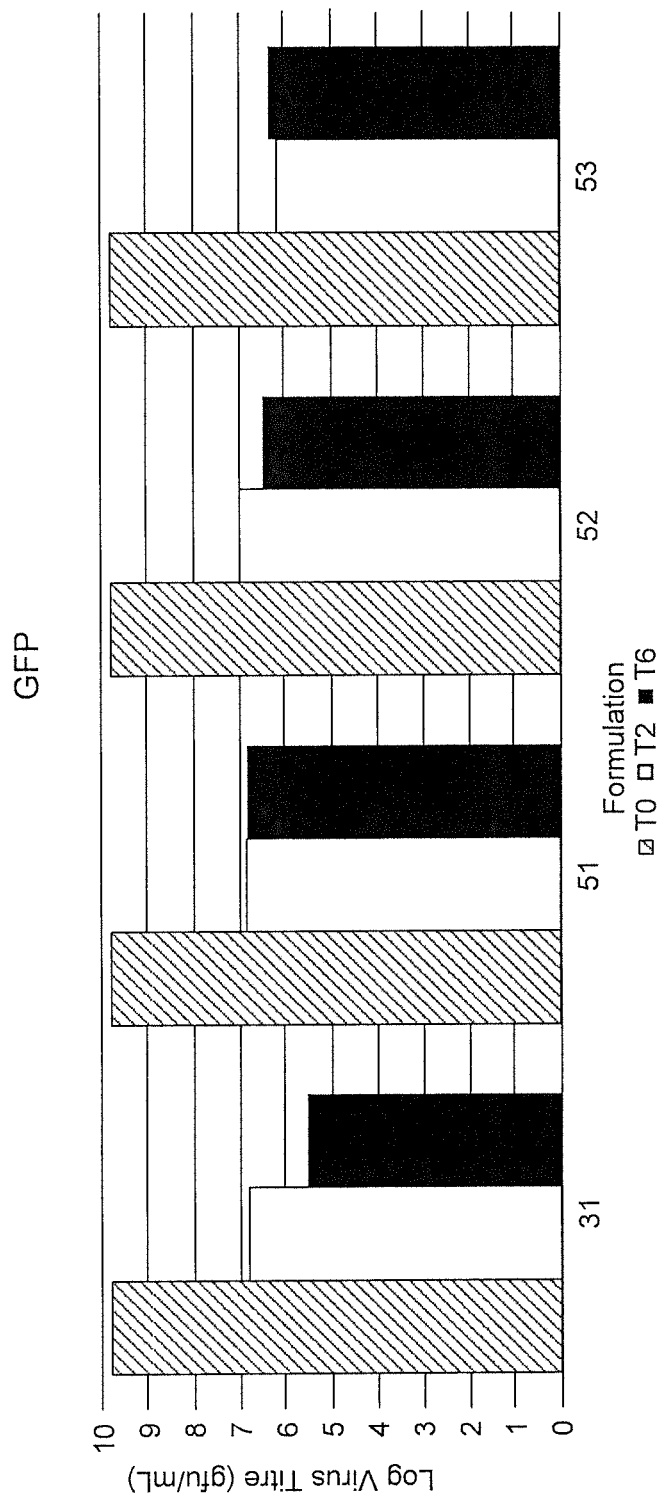

The effect of addition of dextran sulfate, an anionic polymer, on the stability of adenovirus was examined with two experiments (Table 6). In the first experiment, Ad5CD80 system was used. Formulation 51 was formulated with 5 mg/mL dextran sulfate with a low average molecular weight (Mw 6500~10000 Da). Formulation 52 was formulated with 5 mg/mL dextran sulfate with a high average molecular weight (Mw 5000000~3000000 Da). Formulation 53 was formulated with 2.5 mg/mL dextran sulfate with a low average molecular weight (Mw 6500~10000 Da) and 2.5 mg/mL dextran sulfate with a high average molecular weight (Mw 5000000~3000000 Da). The FACS assay was used to determine the infectivity of the formulations at T0 (start), T2 (day), and T6 (day). The formulations were incubated at 45° C. FIG. 9A compares the effect from the addition of dextran sulfate on the stability of adenovirus formulations. In the second experiment, Ad5GFP system was used. The FACS assay was used to determine the infectivity of the formulations at T0 (start), T2 (2 days), and T6 (6 days). The formulations were incubated at 45° C. FIG. 9B compares the effect from the addition of dextran sulfate on the stability of adenovirus formulations.

TABLE 9

| FORMULATION NUMBER | Citrate (mM) | Phosphate (mM) | Sucrose (mM) | Dextran (low) (mg/mL) | Dextran (high) (mg/mL) | pH |
|---|---|---|---|---|---|---|
| 31 | 5 | 5 | 300 | | | 7 |
| 51 | 5 | 5 | 300 | 5 | | 7 |
| 52 | 5 | 5 | 300 | | 5 | 7 |
| 53 | 5 | 5 | 300 | 2.5 | 2.5 | 7 |

Example 10—Final Formulations Selected for the Long-Term Stability Trial

Two final formulations of the present invention (Formulation 127 and Formulation 132) were compared with two adenovirus formulations disclosed in U.S. Pat. No. 7,456,009 (Formulation A195) ("Comparative Example 1"; Formulation 138) and U.S. Pat. No. 7,880,097 (Formulation AQF4-4) ("Comparative Example 2"; Formulation 139) in a stability study (Table 10). Both Ad5CD80 and Ad5GFP systems were used. The formulations were incubated at two different temperatures (25° C. and 37° C.). The FACS assay was used to determine the infectivity of the formulations at T0 (start), T14 (37° C., 14 days), T20 (25° C., 20 days), T41 (37° C., 41 days), and T42 (25° C., 42 days).

FIG. 10A compares the infectivity of these formulations with Ad5CD80 system and an incubation temperature of 37° C. At 37° C. after 41 days, Formulations 127 and 132 containing Ad5CD80 lost less than 1.3 log infectivity; whereas Comparative Examples 1 and 2 lost 1.5 log infectivity and 7.65 log infectivity, respectively.

FIG. 10B compares the infectivity of these formulations with Ad5CD80 system and an incubation temperature of 25° C. All formulations lost less than 1 log infectivity.

FIG. 11A compares the infectivity of these formulations with Ad5GFP system and an incubation temperature of 37° C. At 37° C. after 41 days, Formulations 127 and 132 containing Ad5GFP lost less than 1.6 log infectivity; whereas Comparative Examples 1 and 2 had lost 1.8 log infectivity.

FIG. 11B compares the infectivity of these formulations with Ad5GFP system and an incubation temperature of 25° C. All formulations lost less than 1 log infectivity.

These formulations are on the stability trials at 4° C. for twenty-four months, 25° C. for twelve months, and 37° C. for six months. Furthermore, an additional formulation of the present invention is on the long-term stability trials, which contains 12.2 mM TRIS, 12.6 mM Benzoate, 274.5 mM Sucrose, 0.6 mg/mL Polysorbate 80, 5.7 mg/mL Dextran Sulfate (MW 6,500-10,000), and 0.9 mg/mL Dextran Sulfate (MW>500,000).

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. An aqueous formulation comprising an adenovirus vector containing a whole transgene and carboxymethyl cellulose or a salt form thereof at a concentration ranging from about 0.5 mg/mL to about 10 mg/mL.

2. The formulation of claim 1, wherein the carboxymethyl cellulose or salt form thereof is sodium carboxymethyl cellulose and wherein the sodium carboxymethyl cellulose has an average molecular weight between about 20000 Da and about 1000000 Da.

TABLE 10

| | | Sample ID | | | |
|---|---|---|---|---|---|
| | | Formulation 127 | Formulation 132 | Comparative Example 1 | Comparative Example 2 |
| Formulation(s) | | 20 mM TRIS, 8 mM Benzoate, 0.1 mM EDTA, 150 mM Sucrose, 0.6 mg/mL Tween 80, 4 mg/mL Dextran Sulfate (MW 6,500-10,000), 2 mg/mL Dextran Sulfate (MW >500,000), 5 mg/mL Polyvinyl Alcohol, pH 7 | 20 mM TRIS, 5 mM Benzoate, 0.3 mM EDTA, 400 mM Sucrose, 0.2 mg/mL Tween 80, 6 mg/mL Dextran Sulfate (MW 6,500-10,000), 6 mg/mL Dextran Sulfate (MW >500,000), pH 6 | 10 mM Histidine, 10 mM TRIS, 75 mM NaCl, 146 mM Sucrose, 0.2 mg/mL Tween 80, 1 mM MgCl$_2$, 0.5 v/v Ethanol at pH 7.4. | 10 mM TRIS, 150 mM NaCl, 146 mM Sucrose, 0.1 mg/mL Tween 80, 1 mM MgCl$_2$, 274.76 mM Mannitol at pH 8.2. |
| Log loss of infectivity (FACS) | T0 | 0 | 0 | 0 | 0 |
| | T14 (37° C., 14 days) | 1.36 (CD80) 1.28 (GFP) | 0.2 (CD80) 1.62 (GFP) | 0.6 (CD80) 1.54 (GFP) | 1 (CD80) 1.34 (GFP) |
| | T20 (25° C., 20 days) | 0.2 (CD80) | −1.24 (CD80) | −0.2 (CD80) | −0.46 (CD80) |
| | T41 (37° C., 41 days) | 1.26 (CD80) 1.3 (GFP) | 0 (CD80) 1.6 (GFP) | 1.48 (CD80) 1.76 (GFP) | 7.65 (CD80) 1.79 (GFP) |
| | T42 (25° C., 42 days) | 0.6 (CD80) 0.4 (GFP) | −0.92 (CD80) 0.69 (GFP) | −0.15 (CD80) 0.7 (GFP) | −0.15 (CD80) 0.3 (GFP) |

CONCLUSION

These examples illustrate possible embodiments of the present invention. While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

It is to be appreciated that the Detailed Description section, and not the Summary and Abstract sections, is intended to be used to interpret the claims. The Summary and Abstract sections can set forth one or more, but not all exemplary embodiments of the present invention as contemplated by the inventor(s), and thus, are not intended to limit the present invention and the appended claims in any way.

3. The formulation of claim 2, wherein the sodium carboxymethyl cellulose has an average molecular weight of about 90000 Da.

4. The formulation of claim 1, further comprising at least one displaced buffer having an ionizable group with a pKa value at least one unit higher or lower than the pH of the formulation and having no ionizable group with a pKa value within one unit of the pH of the formulation.

5. The formulation of claim 4, wherein the displaced buffer is selected from the group consisting of tris(hydroxymethyl)aminomethane (TRIS), benzoate ion, and a combination thereof.

6. The formulation of claim 1, wherein the pH of the formulation is between 5 and 8.

7. The formulation of claim 1, further comprising a tonicity modifier selected from the group consisting of 1,2-propanediol, glycerol, mannitol, sorbitol, sucrose, lactose, maltose, and trehalose.

8. The formulation of claim 1, further comprising a non-ionic surfactant selected from the group consisting of a polysorbate and a poloxamer.

9. The formulation of claim 1, further comprising ethylenediaminetetraacetic acid anion (EDTA).

10. The formulation of claim 1, further comprising at least one salt of a divalent cation selected from the group consisting of $MgCl_2$, $MgSO_4$, $CaCl_2$, $CaSO_4$, $ZnCl_2$, $ZnSO_4$, $MnCl_2$, and $MnSO_4$.

11. The formulation of claim 1, further comprising polyvinyl alcohol (PVA).

12. An aqueous formulation comprising either:
(i) an adenovirus vector containing a whole transgene; carboxymethyl cellulose or a salt form thereof at a concentration ranging from about 0.5 mg/mL to about 10 mg/mL; and a combination of TRIS and benzoate ion; and EDTA; wherein the pH of the formulation is about 7; or
(ii) an adenovirus vector containing a whole transgene; carboxymethyl cellulose or a salt form thereof at a concentration ranging from about 0.5 mg/mL to about 10 mg/mL; and a combination of phosphate and citrate ion; wherein the pH of the formulation is about 7.

13. The formulation of claim 1, wherein the formulation loses less than 1 log infectivity of the starting infectivity when stored for 91 hours at 40° C.

14. The formulation of claim 13, wherein the log infectivity is measured by a Fluorescence Activated Cell Sorter (FACS) assay or by a Tissue Culture Infectious Dose 50 ($TCID_{50}$) assay.

15. The formulation of claim 1, wherein the formulation is a pharmaceutical formulation suitable for administration by injection or infusion.

16. A method for the preparation of a storage stable adenovirus vector aqueous liquid formulation, comprising: forming a mixture of an adenovirus vector containing a whole transgene and carboxymethyl cellulose or a salt form thereof at a concentration ranging from about 0.5 mg/mL to about 10 mg/mL.

17. The formulation of claim 1, wherein the adenovirus vector is a human adenovirus.

18. The formulation of claim 17, wherein the human adenovirus is an Ad5 serotype or an Ad35 serotype.

19. The formulation of claim 12, wherein the adenovirus vector is a human adenovirus.

20. The formulation of claim 19, wherein the human adenovirus is an Ad5 serotype or an Ad35 serotype.

21. The method of claim 16, wherein the adenovirus vector is a human adenovirus.

22. The method of claim 21, wherein the human adenovirus is an Ad5 serotype or an Ad35 serotype.

* * * * *